(12) United States Patent
Kirkpatrick

(10) Patent No.: US 11,381,902 B2
(45) Date of Patent: *Jul. 5, 2022

(54) EARPIECE INTRA-AURICULAR SUPPORT SYSTEM

(71) Applicant: Decibullz LLC, Fort Collins, CO (US)

(72) Inventor: Kyle J Kirkpatrick, Fort Collins, CO (US)

(73) Assignee: Decibullz LLC, Fort Collins, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/953,806

(22) Filed: Nov. 20, 2020

(65) Prior Publication Data

US 2021/0084398 A1 Mar. 18, 2021

Related U.S. Application Data

(63) Continuation of application No. 16/661,253, filed on Oct. 23, 2019, now Pat. No. 10,856,065, which is a continuation of application No. 16/198,459, filed on Nov. 21, 2018, now Pat. No. 10,462,552, which is a continuation of application No. 15/411,901, filed on Jan. 20, 2017, now Pat. No. 10,149,038.

(51) Int. Cl.
  *H04R 1/10* (2006.01)
  *A61F 11/12* (2006.01)
  *A61F 11/08* (2006.01)

(52) U.S. Cl.
  CPC .............. *H04R 1/105* (2013.01); *A61F 11/08* (2013.01); *A61F 11/12* (2013.01); *H04R 1/1066* (2013.01); *A61F 11/085* (2022.01); *H04R 1/1016* (2013.01); *H04R 2420/07* (2013.01)

(58) Field of Classification Search
  CPC .... A61F 11/12; A61F 2011/085; H04R 1/105; H04R 1/1016; H04R 1/1066; H04R 2420/07; H04R 25/659
  See application file for complete search history.

(56) References Cited

U.S. PATENT DOCUMENTS

| | | |
|---|---|---|
| 516,135 A | 3/1894 | Thamm |
| 904,715 A | 11/1908 | McWilliams |
| 1,340,512 A | 5/1920 | Wild |
| 2,377,739 A | 6/1945 | Wyckoff |

(Continued)

FOREIGN PATENT DOCUMENTS

| | | |
|---|---|---|
| CA | 100610 | 10/2003 |
| CN | 101073288 A | 11/2007 |

(Continued)

OTHER PUBLICATIONS

Corresponding Chinese Patent Application No. 201880007453.3; Office Action dated Jan. 26, 2021, 10 pages.

(Continued)

*Primary Examiner* — Brian Ensey
(74) *Attorney, Agent, or Firm* — Craig R. Miles; CR Miles P.C.

(57) ABSTRACT

An earpiece including an intra-auricular support, a projection element coupled thereto, and a flexible body disposed thereon and inside an external ear canal of an ear, and a moldable earpiece material moldable about the intra-auricular support to conform to the auricle of an ear and curable to provide a fixed configuration of the earpiece.

28 Claims, 31 Drawing Sheets

(56) References Cited

U.S. PATENT DOCUMENTS

| | | | |
|---|---|---|---|
| 2,430,229 | A | 11/1947 | Kelsey |
| 2,521,414 | A | 9/1950 | Schier |
| 2,729,376 | A | 1/1956 | Gould et al. |
| 2,881,759 | A | 4/1959 | Hocks et al. |
| D185,740 | S | 7/1959 | Criswell |
| 3,068,954 | A | 12/1962 | Strzalkowski |
| 3,112,668 | A | 12/1963 | Moshay |
| D206,665 | S | 1/1967 | Sanzone |
| D208,784 | S | 10/1967 | Sanzone |
| 3,415,246 | A | 12/1968 | Hill |
| 3,440,365 | A | 4/1969 | Bryant et al. |
| D215,138 | S | 9/1969 | Makey |
| 3,810,812 | A | 5/1974 | Koenig |
| D250,033 | S | 10/1978 | Stein |
| D266,271 | S | 9/1982 | Johanson et al. |
| D266,590 | S | 10/1982 | Bennett |
| 4,412,096 | A | 10/1983 | Edgerton et al. |
| D278,363 | S | 4/1985 | Schenkel et al. |
| 4,537,187 | A | 8/1985 | Scott |
| 4,579,112 | A | 4/1986 | Scott |
| D290,203 | S | 6/1987 | Berry, Jr. |
| 4,702,238 | A | 10/1987 | Scott |
| 4,870,688 | A | 9/1989 | Vorova et al. |
| 4,880,076 | A | 11/1989 | Ahlberg et al. |
| 4,965,838 | A | 10/1990 | Kamon et al. |
| 5,002,151 | A | 3/1991 | Oliveira et al. |
| 5,048,092 | A | 9/1991 | Yamagishi et al. |
| 5,185,802 | A | 2/1993 | Stanton |
| 5,321,757 | A | 6/1994 | Woodfill, Jr. |
| 5,659,156 | A | 8/1997 | Mauney et al. |
| 5,676,068 | A | 10/1997 | Kallander |
| 5,711,313 | A | 1/1998 | Fleming |
| 5,718,244 | A | 2/1998 | Thornton |
| 5,753,781 | A * | 5/1998 | Oxman .................. A61K 6/90 523/120 |
| 5,881,159 | A | 3/1999 | Aceti et al. |
| 5,950,794 | A | 9/1999 | Porco et al. |
| 6,082,485 | A | 7/2000 | Smith |
| 6,122,388 | A | 9/2000 | Feldman |
| 6,301,367 | B1 | 10/2001 | Boyden et al. |
| 6,310,961 | B1 | 10/2001 | Oliveira et al. |
| 6,354,990 | B1 | 3/2002 | Juneau et al. |
| 6,434,248 | B1 | 8/2002 | Juneau et al. |
| 6,445,865 | B1 | 9/2002 | Janus et al. |
| 6,511,732 | B1 | 1/2003 | Chao |
| 6,595,317 | B1 | 7/2003 | Widmer et al. |
| 6,688,421 | B2 | 2/2004 | Dyer et al. |
| 6,690,807 | B1 | 2/2004 | Meyer |
| 6,761,789 | B2 | 7/2004 | Juneau et al. |
| D505,132 | S | 5/2005 | Linville et al. |
| D527,056 | S | 8/2006 | Manville |
| 7,130,437 | B2 | 10/2006 | Stonikas et al. |
| D535,642 | S | 1/2007 | Garcia et al. |
| 7,217,335 | B2 | 5/2007 | Juneau et al. |
| D550,202 | S | 9/2007 | Meier et al. |
| 7,403,629 | B1 | 7/2008 | Aceti |
| D593,076 | S | 5/2009 | Kung et al. |
| 7,627,131 | B2 | 12/2009 | Nielsen et al. |
| 7,628,366 | B2 | 12/2009 | Scott |
| D622,265 | S | 8/2010 | Rye |
| 7,778,434 | B2 | 8/2010 | Juneau et al. |
| 7,889,883 | B2 | 2/2011 | Cartwright et al. |
| D635,547 | S | 4/2011 | Komiyama |
| D645,458 | S | 9/2011 | Silvestri et al. |
| 8,027,638 | B2 | 9/2011 | Sanguino et al. |
| D647,514 | S | 10/2011 | Wikel et al. |
| D655,693 | S | 3/2012 | Silvestri et al. |
| D656,129 | S | 3/2012 | Kelly et al. |
| 8,184,838 | B2 * | 5/2012 | Solomito ............. H04R 1/1016 381/322 |
| 8,201,561 | B2 | 6/2012 | Blanchard |
| D667,817 | S | 9/2012 | Otani |
| 8,280,093 | B2 | 10/2012 | Siahaan et al. |
| 8,657,064 | B2 | 2/2014 | Staab et al. |
| D716,770 | S | 11/2014 | Bonahoom et al. |
| D721,354 | S | 1/2015 | Thompson et al. |
| 8,931,489 | B2 | 1/2015 | Smith |
| D729,764 | S | 5/2015 | Arjomand |
| D735,169 | S | 7/2015 | Shieh |
| 9,179,211 | B2 | 11/2015 | Kirkpatrick |
| D744,456 | S | 12/2015 | Pedersen |
| D752,026 | S | 3/2016 | Yang |
| D754,638 | S | 4/2016 | Krissman |
| D758,355 | S | 6/2016 | Lee et al. |
| D759,633 | S | 6/2016 | Gondo |
| 9,451,353 | B2 | 9/2016 | Kirkpatrick |
| D773,440 | S | 12/2016 | Pedersen |
| D773,441 | S | 12/2016 | Pedersen |
| 9,628,889 | B2 | 4/2017 | Kirkpatrick |
| D814,443 | S | 4/2018 | Sandanger |
| D828,826 | S | 9/2018 | Schaal |
| D832,240 | S | 10/2018 | Birger |
| D835,077 | S | 12/2018 | Aoyagi et al. |
| 10,149,038 | B2 | 12/2018 | Kirkpatrick |
| D838,693 | S | 1/2019 | Fu |
| D839,243 | S | 1/2019 | Smith et al. |
| D845,282 | S | 4/2019 | Chen |
| D850,417 | S | 6/2019 | Yang |
| D859,368 | S | 9/2019 | Huang |
| D860,172 | S | 9/2019 | Yun |
| 10,462,552 | B2 | 10/2019 | Kirkpatrick |
| D866,532 | S | 11/2019 | Zhang et al. |
| D869,444 | S | 12/2019 | Tang |
| D870,079 | S | 12/2019 | Yun |
| D871,374 | S | 12/2019 | Karayiannis et al. |
| D871,376 | S | 12/2019 | Zhou |
| D875,071 | S | 2/2020 | Wei et al. |
| D879,748 | S | 3/2020 | Lee |
| D881,163 | S | 4/2020 | Duddy et al. |
| D881,164 | S | 4/2020 | Luo |
| D881,849 | S | 4/2020 | Aoyagi et al. |
| D883,262 | S | 5/2020 | Wu |
| D883,959 | S | 5/2020 | Lee |
| D892,085 | S | 8/2020 | Kim |
| D892,089 | S | 8/2020 | Karayiannis et al. |
| D894,158 | S | 8/2020 | Gu |
| D895,572 | S | 9/2020 | Maeda et al. |
| D895,581 | S | 9/2020 | Wu |
| D897,995 | S | 10/2020 | Duddy et al. |
| 10,805,747 | B2 | 10/2020 | Thumm et al. |
| D902,890 | S | 11/2020 | Williamson et al. |
| D914,650 | S | 3/2021 | Hu |
| D925,493 | S | 7/2021 | Kirkpatrick |
| 2001/0043708 | A1 | 11/2001 | Brimhall |
| 2003/0048916 | A1 | 3/2003 | Chen |
| 2003/0099370 | A1 | 5/2003 | Moore |
| 2005/0147269 | A1 | 7/2005 | Oliveira et al. |
| 2006/0098833 | A1 | 5/2006 | Juneau et al. |
| 2006/0177082 | A1 | 8/2006 | Solomito et al. |
| 2008/0187161 | A1 | 8/2008 | Tiemens et al. |
| 2008/0298626 | A1 | 12/2008 | Dean |
| 2009/0028356 | A1 | 1/2009 | Ambrose et al. |
| 2009/0041287 | A1 * | 2/2009 | Quinlisk ............. H04R 1/1058 381/380 |
| 2009/0141923 | A1 | 6/2009 | Smith |
| 2009/0190786 | A1 | 7/2009 | Miskiel et al. |
| 2009/0214072 | A1 | 8/2009 | Staab et al. |
| 2009/0232342 | A1 | 9/2009 | Oliveira |
| 2009/0252362 | A1 | 10/2009 | Ooi et al. |
| 2010/0086158 | A1 | 4/2010 | Oberlander |
| 2011/0255729 | A1 | 10/2011 | Tan et al. |
| 2012/0057739 | A1 | 3/2012 | Smith et al. |
| 2012/0189146 | A1 | 7/2012 | Wuidart |
| 2012/0243701 | A1 | 9/2012 | Parkins et al. |
| 2013/0216086 | A1 | 8/2013 | Kirkpatrick |
| 2014/0119589 | A1 | 5/2014 | Wyzisk et al. |
| 2015/0146909 | A1 | 5/2015 | Kirkpatrick |
| 2015/0382123 | A1 | 12/2015 | Jobani |
| 2016/0014493 | A1 | 1/2016 | Chen |
| 2016/0073193 | A1 | 3/2016 | Kirkpatrick |
| 2016/0373852 | A1 | 12/2016 | Kirkpatrick |
| 2017/0238083 | A1 * | 8/2017 | Smith .................. H04R 1/105 381/381 |
| 2017/0311069 | A1 * | 10/2017 | Prevoir ............. H04R 1/1058 |

(56) References Cited

U.S. PATENT DOCUMENTS

| | | | |
|---|---|---|---|
| 2019/0261079 | A1 | 8/2019 | Okawa et al. |
| 2020/0029161 | A1 | 1/2020 | Thumm et al. |
| 2020/0059715 | A1 | 2/2020 | Hsiao |

FOREIGN PATENT DOCUMENTS

| | | |
|---|---|---|
| CN | 104160719 A | 11/2014 |
| CN | 304145346 | 5/2017 |
| CN | 304301289 | 9/2017 |
| EP | 0895703 | 2/1999 |
| EP | 1032243 | 8/2000 |
| EP | 2107827 | 10/2009 |
| GB | 2470177 | 11/2010 |
| IN | 298802-0001 | 10/2017 |
| JP | 2020053853 A | 4/2020 |
| WO | WO 1992/003894 | 3/1992 |
| WO | WO 1999/031935 | 6/1999 |
| WO | WO 00/42817 | 7/2000 |
| WO | WO 2012/024656 | 2/2012 |
| WO | WO 2018/099562 A1 | 7/2018 |

OTHER PUBLICATIONS

U.S. Appl. No. 61/596,567, filed Feb. 8, 2012.
PCT Interanational Patent Application No. PCT/US2013/025288; ISR dated Jun. 2, 2013, 11 total pages.
Design U.S. Appl. No. 29/536,192, filed Aug. 14, 2015.
Angell. PodFitKit for Apple earbuds announced. iLounge, website, http://www.ilounge.com, originally downloaded Dec. 31, 2012, 4 total pages.
E-Bay. New SUGRU Black 3 pack Moldable Self Setting Rubber Customize Your Earbuds. Website, http://www.ebay.com, originally downloaded Dec. 31, 2012, 4 total pages.
Fuze Custom Earphones. On-line Catalog, http://www.earfuze.com, originally downloaded Dec. 31, 2012, 1 page.
How-to Geek. How to Make Custom Silicone Ear Molds for Your In-Ear Monitors. Website, http://www.howtogeek.com, originally downloaded Dec. 31, 2012, 20 total pages.
Lloyds. Custom Ear Mold—Standard. On-line Catalog, http://lloydhearingaid.com, originally downloaded Dec. 31, 2012, 1 page.
mylobie.com. Lobies—comfortable earbuds adapters for iPod, iPhone, and portable audio.Website, http://www.mylobie.com, originally downloaded Dec. 31, 2012, 1 page.
Zapconnect. Hearing Aid Moldable Impression Silicone Putty. Website, http://www.zapconnect.com, originally downloaded Dec. 31, 2012, 1 page.
Zenplugs Moulded Earplug Shop. Zenpods Blue Molded Earphone Adaptors . . . On-line Catalog, http://shop.zenplugs.com, originally downloaded Dec. 24, 2013, 1 page.
FLUGZ. Advanced Hearing Protection. Website, https://www.flugz.com, originally downloaded Aug. 17, 2015, 15 pages total.
FLUGZ. Form and Fit. Website, https://www.flugz.com, originally downloaded Aug. 17, 2015, 3 pages total.
FLUGZ. Why FLUGZ. Website, https://www.flugz.com, originally downloaded Aug. 17, 2015, 3 pages total.
FLUGZ. Advanced Hearing Protection. Website, https://www.flugz.com, originally downloaded Aug. 17, 2015, 2 pages total.
European Patent Application No. 13746012.7; European Search Report, dated Jan. 27, 2016, 6 pages total.
Chinese Patent Application No. 201380013425.X; Office Action and Search Report dated Oct. 8, 2016, 8 pages total.
European Patent Application No. 13746012.7; Office Action dated Nov. 18, 2016, 5 pages total.
U.S. Appl. No. 15/481,983, filed Apr. 7, 2017.
Design U.S. Appl. No. 29/599,445, filed Apr. 3, 2017.
What Hi-Fi? Dog & Bone earphones include a heating dock to provide a better fit for your earbuds. Website, http://www.whathifi.com, originally downloaded Feb. 10, 2017, total 5 pages.
Sunshine Coast Daily. Earmade: the little QLD idea on world stage. Website, https://www.sunshinecoastdaily.com.au, total 6 pages.
Chinese Patent Application No. 201380013425.X; 2nd Office Action dated Mar. 31, 2017, 8 pages total.
Chinese Patent Application No. 201380013425.X; 3d Office Action dated Aug. 2, 2017, 7 pages total.
PCT International Patent Application No. PCT/US18/12653; International Search Report and Written Opinion of the International Searching Authority dated Mar. 19, 2018, 12 pages.
Wacker. Wacker silicone elastomers: Purity and Future Proof. Mar. 2014. Retrieved from the Internet: <URL: https://www.ringierevents.cn/eve_files/files/4db83d3c99c44bl8b6b9d38f23a0ac98.pdf>, retrieved Mar. 2, 2018, 35 pages.
U.S. Appl. No. 16/127,120, Office Action dated Feb. 4, 2020.
Corresponding Australian Patent Application No. 2018210187, Examination Report No. 1 dated Apr. 17, 2020.
Corresponding Chinese Patent Application No. 201880007453.3; Office Action dated Jun. 1, 2020, 11 pages.
PCT International Patent Application No. PCT/US20/23527; International Search Report and Written Opinion of the International Searching Authority dated Jun. 19, 2020, 11 pages.
U.S. Appl. No. 16/465,652; Office Action dated Jan. 22, 2020.
U.S. Appl. No. 16/465,652; Notice of Allowance dated Jul. 1, 2020.
European Patent Application No. 18741229.1; Extended European Search Report dated Sep. 8, 2020, 12 pages.
Australian Patent Application No. 2018210187; Examination Report No. 2, dated Sep. 23, 2020, 4 pages.
EarBuddyz 2.0 Ear Hooks and Covers Accessories, announced Dec. 14, 2015 [online], retrieved May 5, 2021, retrieved from internet, https://www.amazon.com/EarBuddyz-Accessories-Compalible-Headphones-Earphones/dp/B019BREFE4.
Far End Gear Budloks Earphone Sport Grips, announced Dec. 9, 2015 [online], retrieved May 5, 2021, retrieved from internet, https://www.amazon.com/Far-End-Gear-Budlocks-Earphone/dp/B01950PLKK/ref=asc_df_B01950PLKK/?lag=hyprod-20&linkCode=dto&hvadid=309820150211&hvpos=&hvnetw=g&hvrand=17068762569299593528&hvpone=&hvptwo=&hvqmt=&hvdev=c&hvdvemdl=&hvlocint=&hvlocphy=9008139&hvtargid=pla-592922917164&psc=1.
Earbuds Eargel Earhooks, announced Dec. 26, 2016 [online], retrieved May 5, 2021, retrieved from internet, https://www.amazon.com/Earbuds-Earhooks-Replacement-Ear-Tips-Earhook/dp/B071YZ4F3Y/ref=asc_df_B071YZ4F3Y/?tag=hyprod-20&linkCode=dfO&hvadid=242108112383&hvpos=&hvnetw=g&hvrand=16397304497773344182&hvpone=&hvptwo=&hvqmt=&hvdev=c&hvdvcmdl=&hvlocint=&hvlocphy=9008139&hvlargid=pla-569399210150&psc=1.
ALXCD Silicone Earhooks for Sony, no announcement date [online], retrieved May 5, 2021, retrieved from internet, https://www.pricepulse.app/alxcd-silicone-earhooks-for-sony-mdr-xb510as-mdr-x_us_2278606.
U.S. Appl. No. 29/714,695, Notice of Allowance dated Jun. 10, 2021, 4 pages.

* cited by examiner

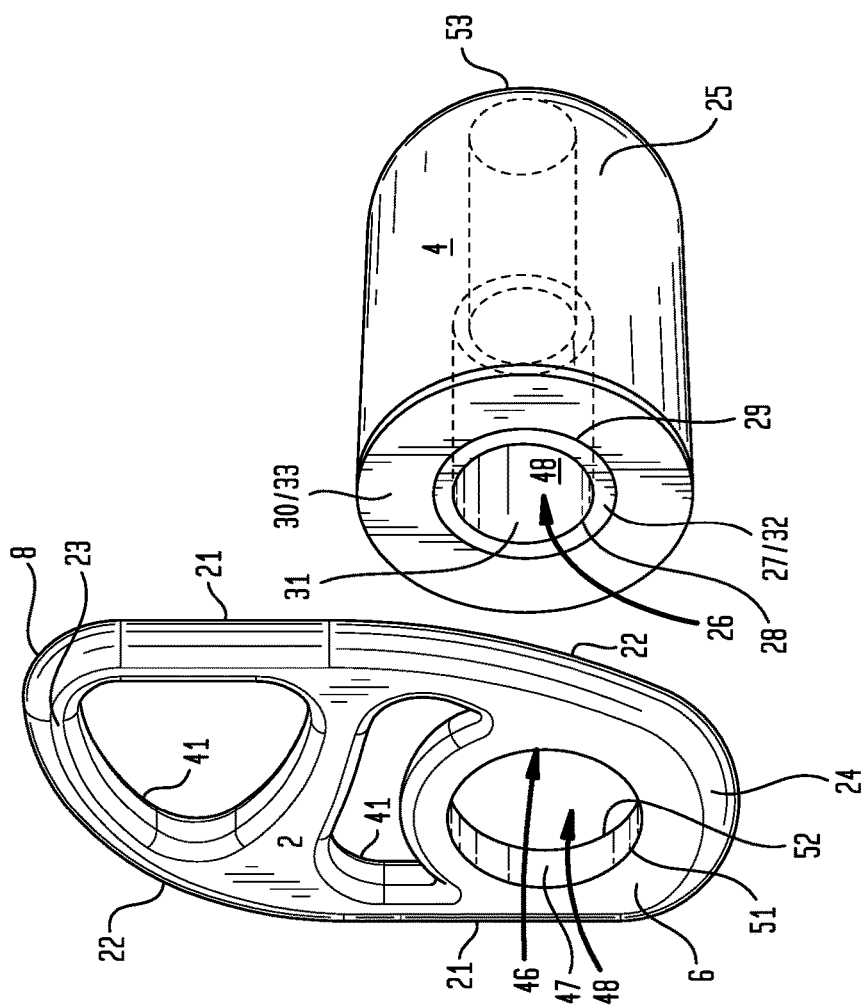
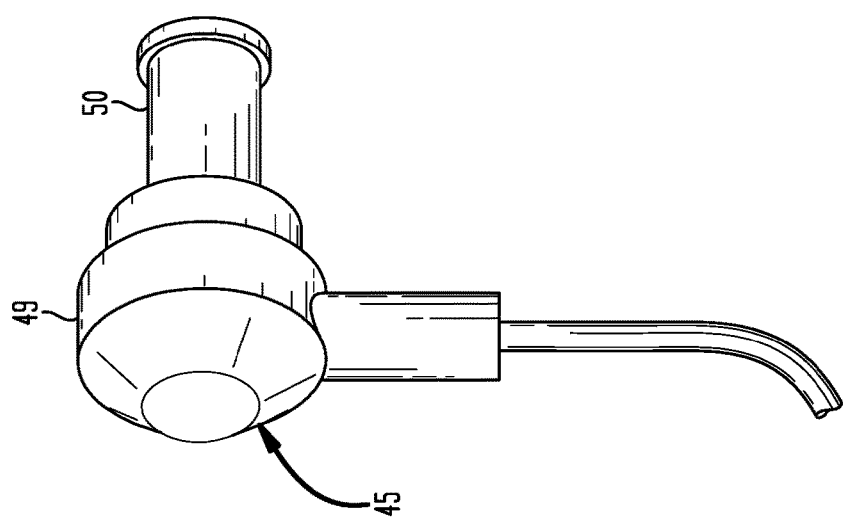
FIG. 19

EARPIECE INTRA-AURICULAR SUPPORT SYSTEM

This United States Patent Application is a continuation of U.S. patent application Ser. No. 16/661,253, filed Oct. 23, 2019, now U.S. Pat. No. 10,856,065, issued Dec. 1, 2020, which is a continuation of U.S. patent application Ser. No. 16/198,459, filed Nov. 21, 2018, now U.S. Pat. No. 10,462,552, issued Oct. 29, 2019, which is a continuation of U.S. patent application Ser. No. 15/411,901, filed Jan. 20, 2017, now U.S. Pat. No. 10,149,038, issued Dec. 4, 2018, hereby incorporated by reference herein.

I. TECHNICAL FIELD

An earpiece including an intra-auricular support positionable in an auricle of an ear, a projection element extending a distance outward of the intra-auricular support, and a flexible body coupled about the projection element and configured to engage an external ear canal of an ear concurrent with the intra-auricular support positioned in the auricle of the ear, and a moldable earpiece material moldable about the intra-auricular support to conform to the auricle of an ear and curable to provide a fixed configuration of the earpiece.

II. BACKGROUND

Because conventional earpieces may not be configured to the auricle of the ear of a wearer, the earpiece may not stay in fixed engagement with the auricle of the ear, or the earpiece may not correctly align with the external ear canal, or the earpiece may be uncomfortable for the wearer to position into or retain in the auricle of the ear.

Additionally, a wide variety of earplugs or in-ear devices to protect against or deliver sound to the ear such as medical equipment, headsets, hearing aids, cellular telephones, and the like, include, in part, in-ear devices such as earphones, earplugs, earbuds, ear tips, ear tubes, or the like, not configured to the auricle of an individual wearer's ear.

The instant invention provides the advantages of a moldable earpiece conformed to the auricle of the wearer's ear, and which can retain or removably retain an in-ear device to overcome in whole or in part certain of the forgoing disadvantages associated with conventional in-ear devices.

III. SUMMARY OF THE INVENTION

Accordingly, a broad object of the invention can be to provide an earpiece, including one or more of: an intra-auricular support engagable to an auricle of an ear, a projection element outwardly extending from the inner surface of the intra-auricular support, a flexible body disposed about the projection element and disposable inside the external ear canal of an ear concurrent with the intra-auricular support engaged with the auricle of the ear, and a moldable earpiece material moldable about the intra-auricular support to conform to the auricle of the ear and curable to provide a fixed configuration of the earpiece.

Another broad object of the invention can be to provide a method of making an earpiece, including one or more of: obtaining an intra-auricular support, coupling a projection element to outwardly extend from the inner surface of the intra-auricular support, disposing a flexible body about the projection element and configured to engage the inside of an external ear canal of an ear, providing a moldable earpiece material capable of molding about the intra-auricular support to conform to the auricle of the ear, and which can further include one or more of: generating a passage communicating between the outer surface of said intra-auricular support and the flexible body second end, and coupling an intra-auricular support conduit configured to removably retain an in-ear device to the intra-auricular support.

Another broad object of the invention can be to provide a method for molding an earpiece, including one or more of: obtaining an intra-auricular support having a projection element outwardly extending from the inner surface, and a flexible body disposed about the projection element, concurrently engaging the intra-auricular support with the auricle of an ear and the flexible body with the external ear canal of an ear, molding a moldable earpiece material about the intra-auricular support to conform to the auricle of the ear and curing the moldable earpiece material to provide a fixed configuration of the earpiece conformed to the auricle of the ear.

Naturally, further objects of the invention are disclosed throughout other areas of the specification, drawings, photographs, and claims.

IV. A BRIEF DESCRIPTION OF THE DRAWINGS

Figure 17:
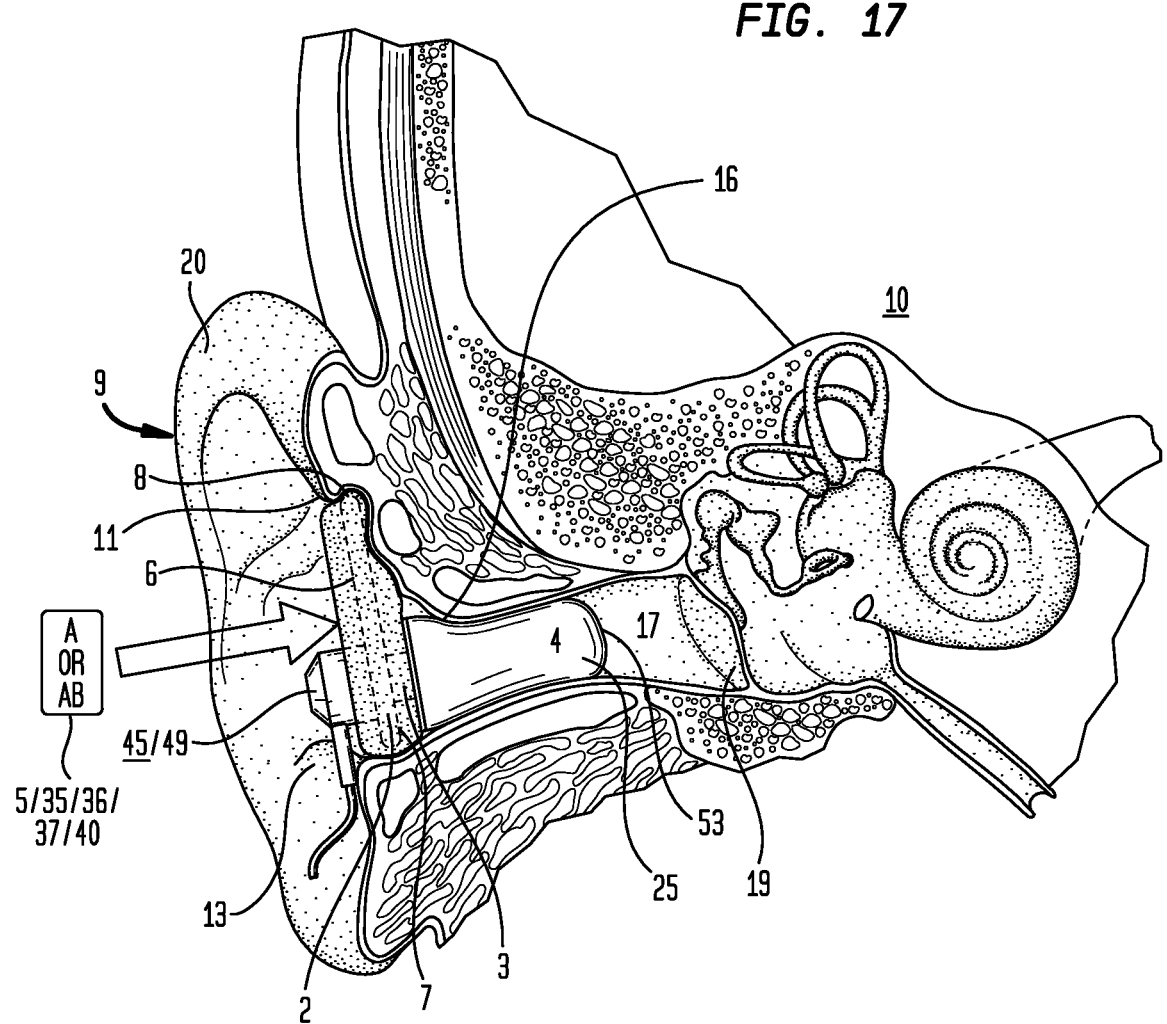

FIG. 17 is a cross sectional side view of the ear and the particular embodiment of an intra-auricular support having the intra-auricular support conduit removably retaining an in-ear device, projection element, and the flexible body coupled about the projection element and engaged with the external ear canal and further illustrating a moldable earpiece material A or AB molded about the intra-auricular support and to the contour of the auricle of the ear to provide a fixed configuration of the earpiece.

Figure 18:
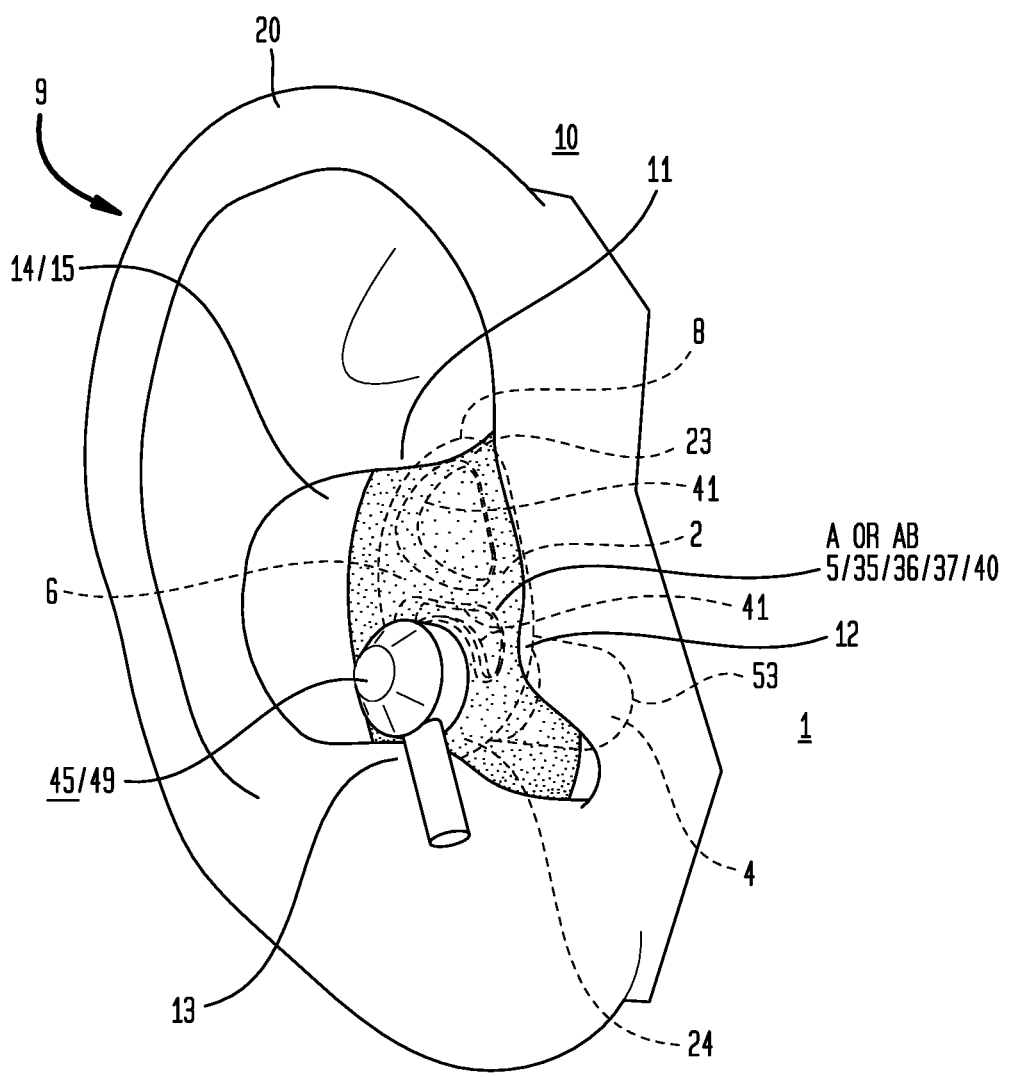

FIG. 18 is a perspective view of the particular embodiment of a fixed configuration of the earpiece retaining an in-ear device in an ear.

FIG. 19 is an exploded view of the particular embodiment of an intra-auricular support having an intra-auricular support conduit configured to removably retain an in-ear device having a body and a sound delivery element with the sound delivery element extendable through the intra-auricular support conduit to provide a projection element, and a flexible body which removably couples to the projection element.

Figure 20:
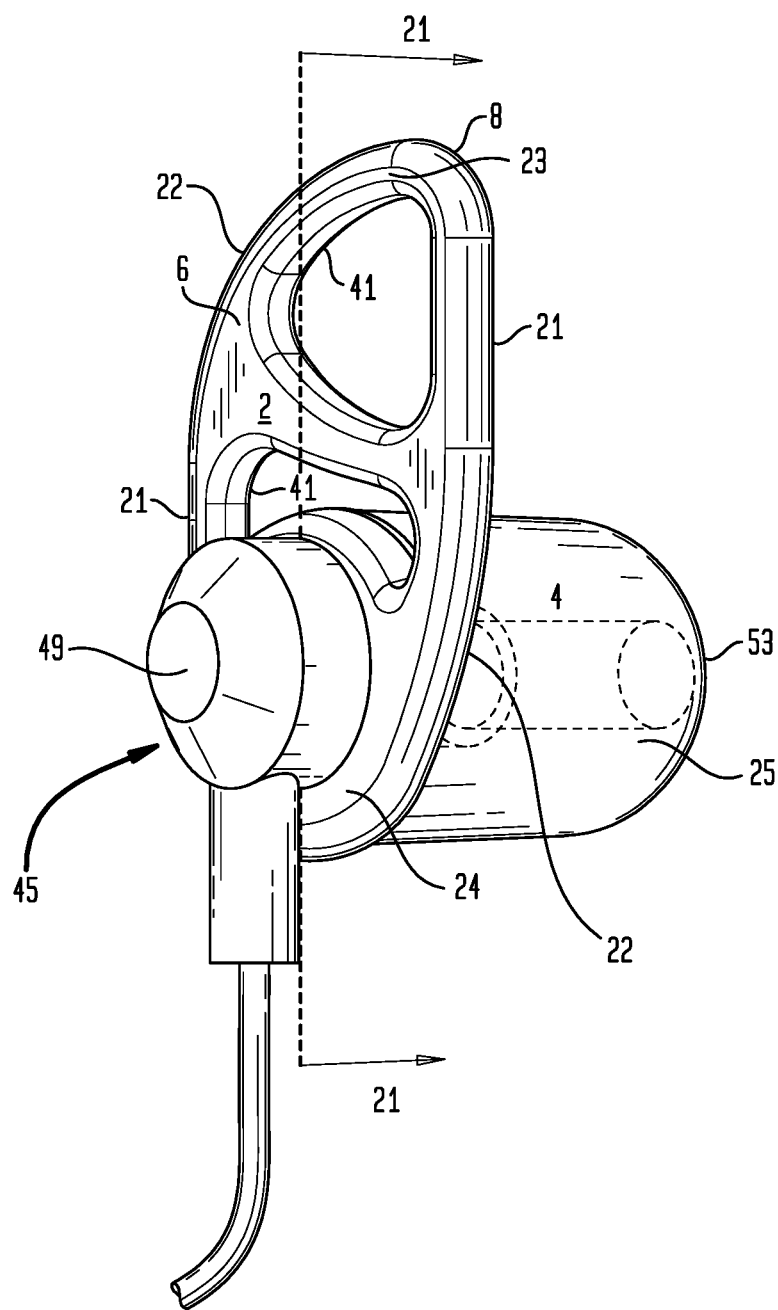

FIG. 20 is a perspective view of the particular embodiment of an intra-auricular support having an intra-auricular support conduit removably retaining an in-ear device having a body and a sound delivery element with the sound delivery element extending outwardly from the intra-auricular support to provide a projection element, and a flexible body which removably couples to the projection element.

Figure 21:
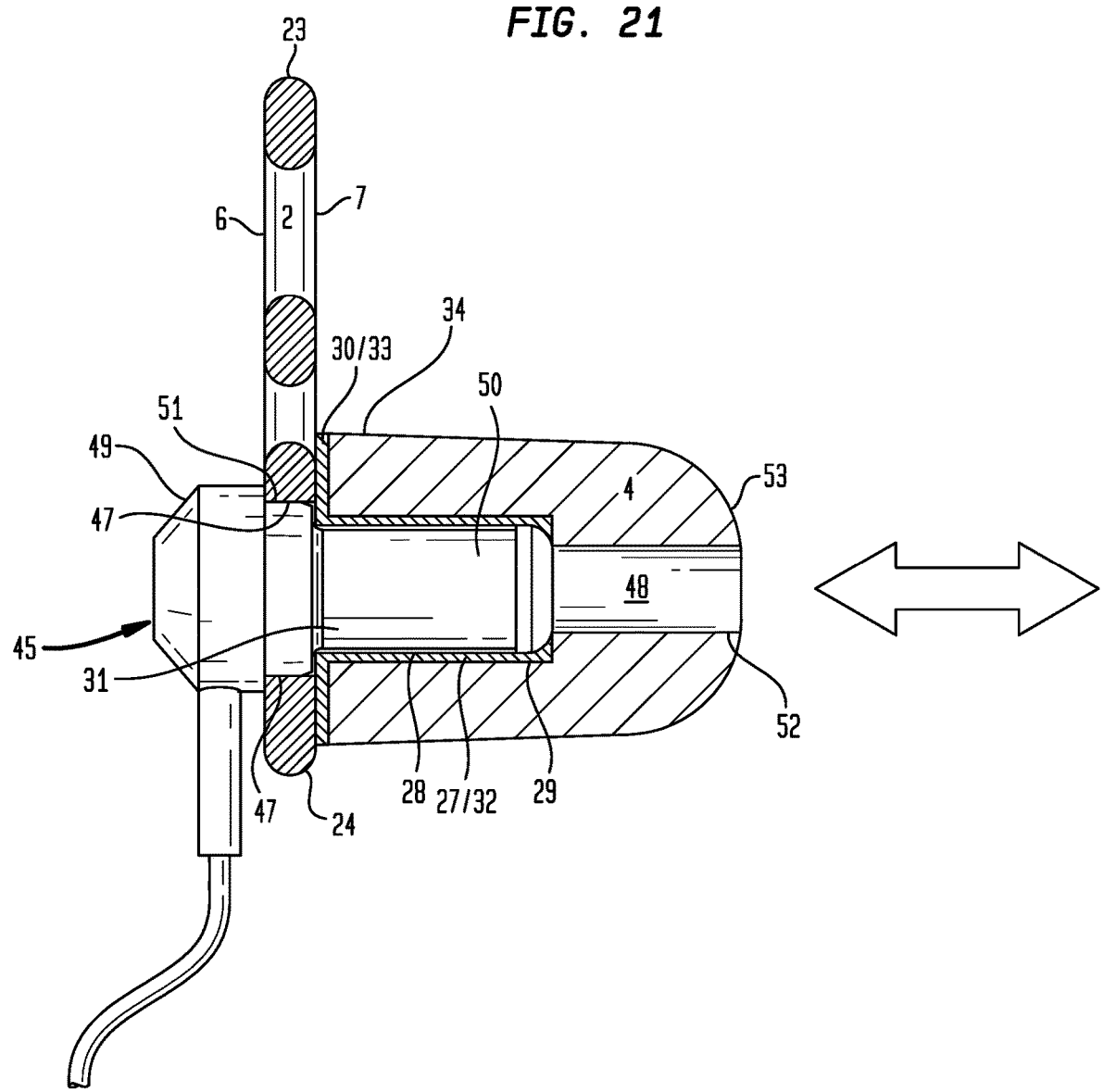

FIG. 21 is a cross sectional side view 21-21 of the particular embodiment of an intra-auricular support having the intra-auricular support conduit retaining an in-ear device with the sound delivery element extending outwardly from the intra-auricular support to provide the projection element, and the flexible body removably coupled to the projection element.

Figure 22:
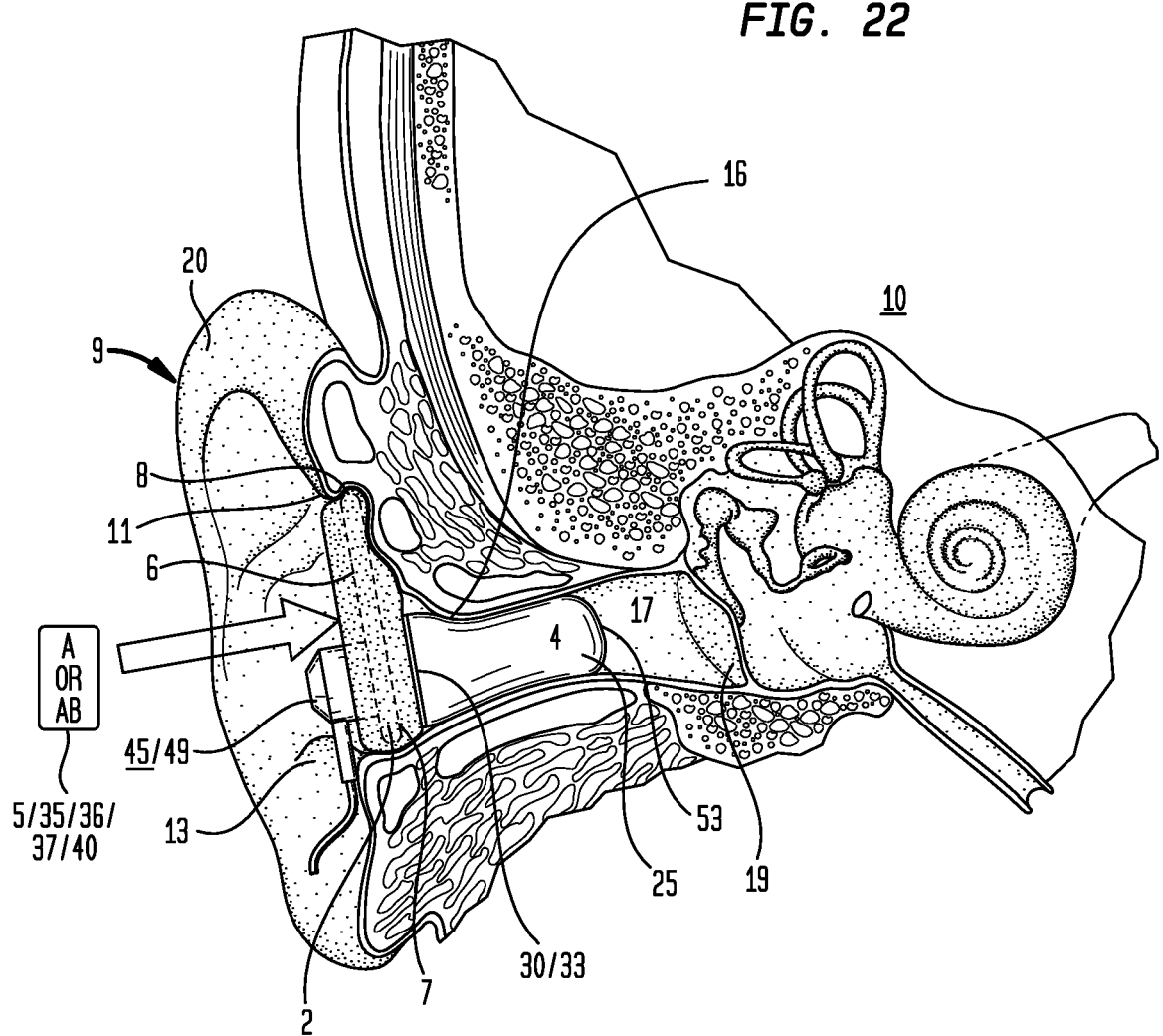

FIG. 22 is a cross sectional side view of the ear and the particular embodiment of an intra-auricular support having the intra-auricular support conduit retaining an in-ear device with the sound delivery element extending outwardly from the intra-auricular support to provide the projection element, and the flexible body engaged with the ear and further illustrating a moldable earpiece material A or AB molded about the intra-auricular support and to the contour of the auricle of the ear to provide a fixed configuration of the earpiece.

Figure 23:
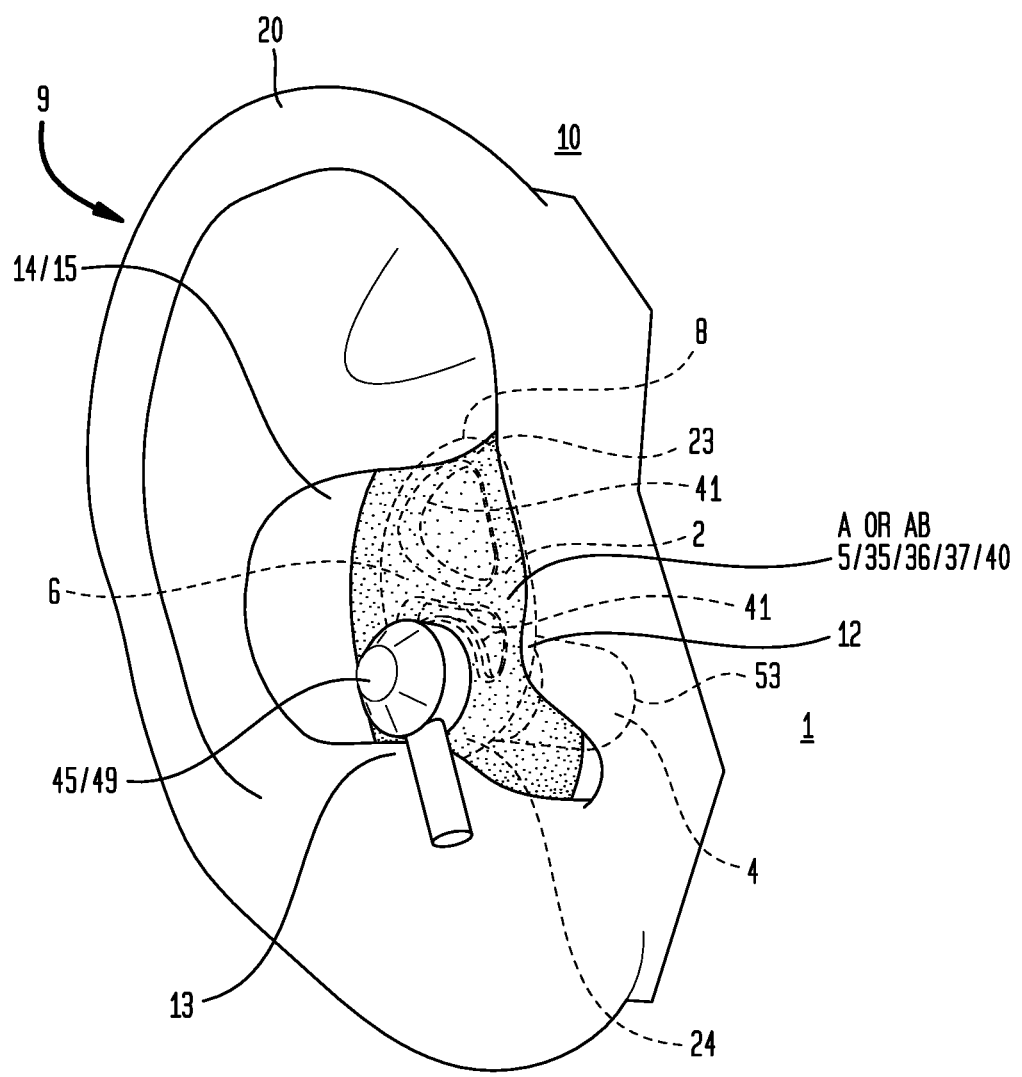

FIG. 23 is a perspective view of the particular embodiment of the fixed configuration of the earpiece in an ear.

Figure 24:
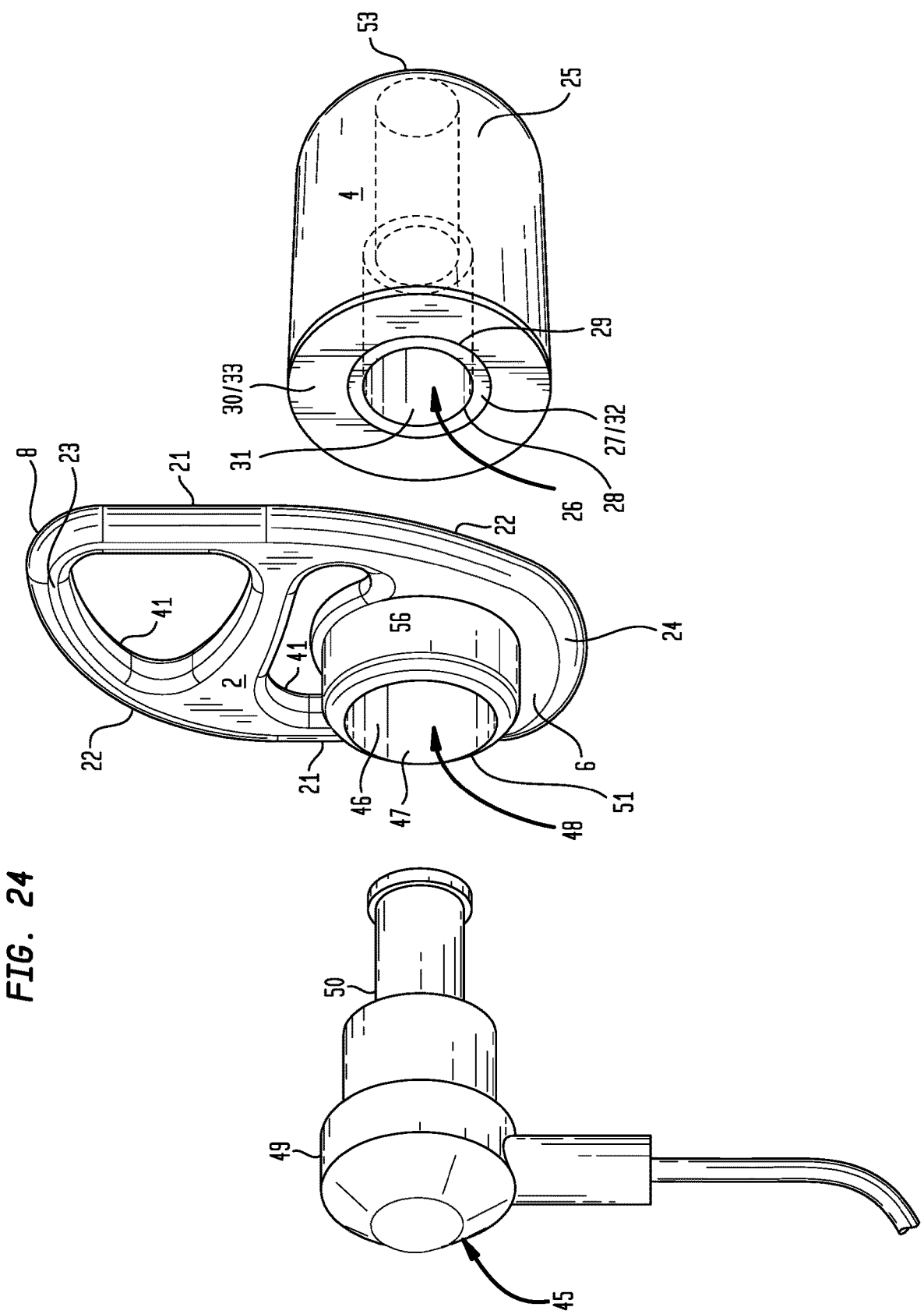

FIG. 24 is an exploded view of a particular embodiment of an intra-auricular support having an intra-auricular support conduit which extends a distance outwardly from the outer surface of the intra-auricular support and configured to removably retain an in-ear device having a body and a sound delivery element with the sound delivery element extendable outwardly from the inner surface of the intra-auricular support to provide a projection element, and a flexible body which removably couples to the projection element.

Figure 25:
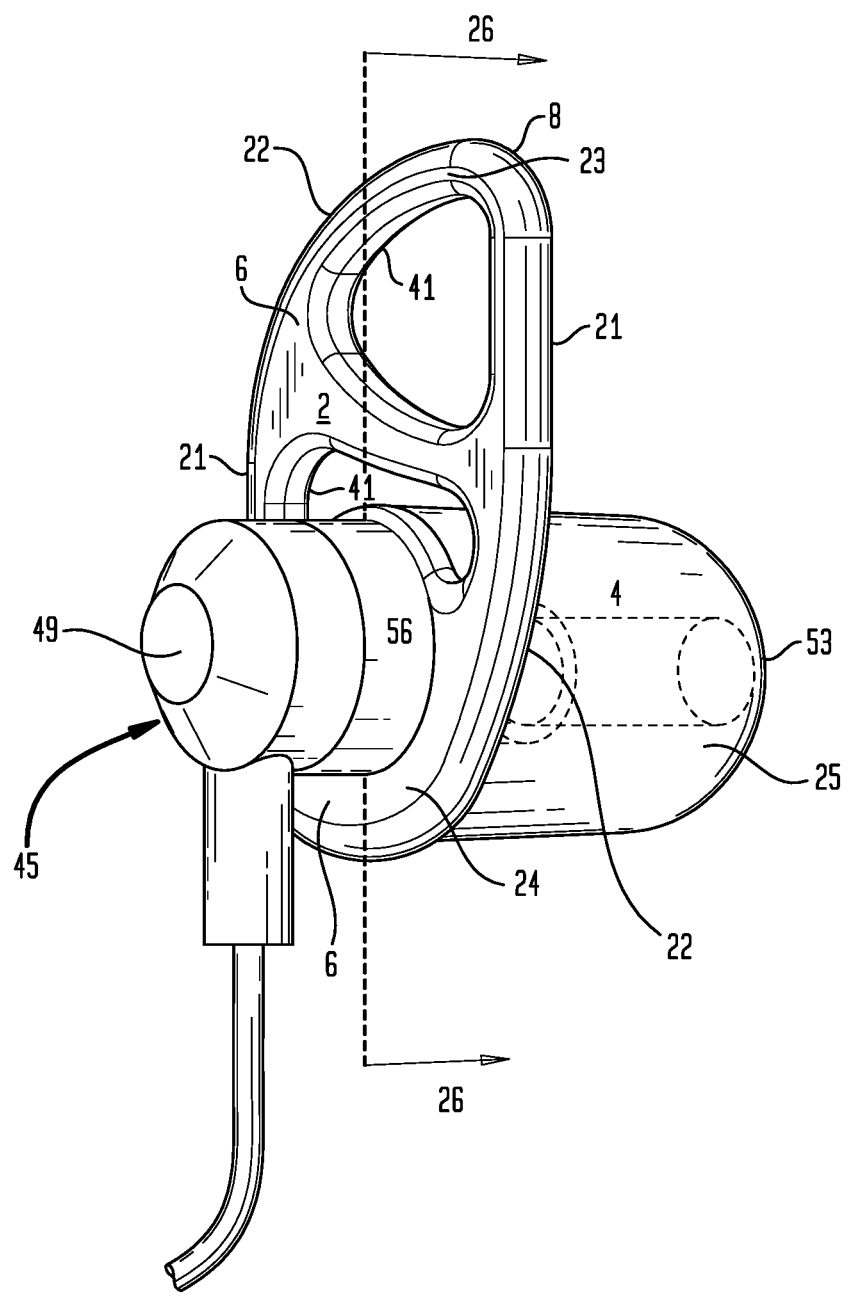

FIG. 25 is a perspective view of a particular embodiment of an intra-auricular support having an intra-auricular support conduit which extends a distance outwardly from the outer surface of the intra-auricular support and removably retaining an in-ear device having a body and a sound delivery element extending outwardly from the inner surface of the intra-auricular support to provide a projection element, and a flexible body which removably coupled to the projection element.

Figure 26:
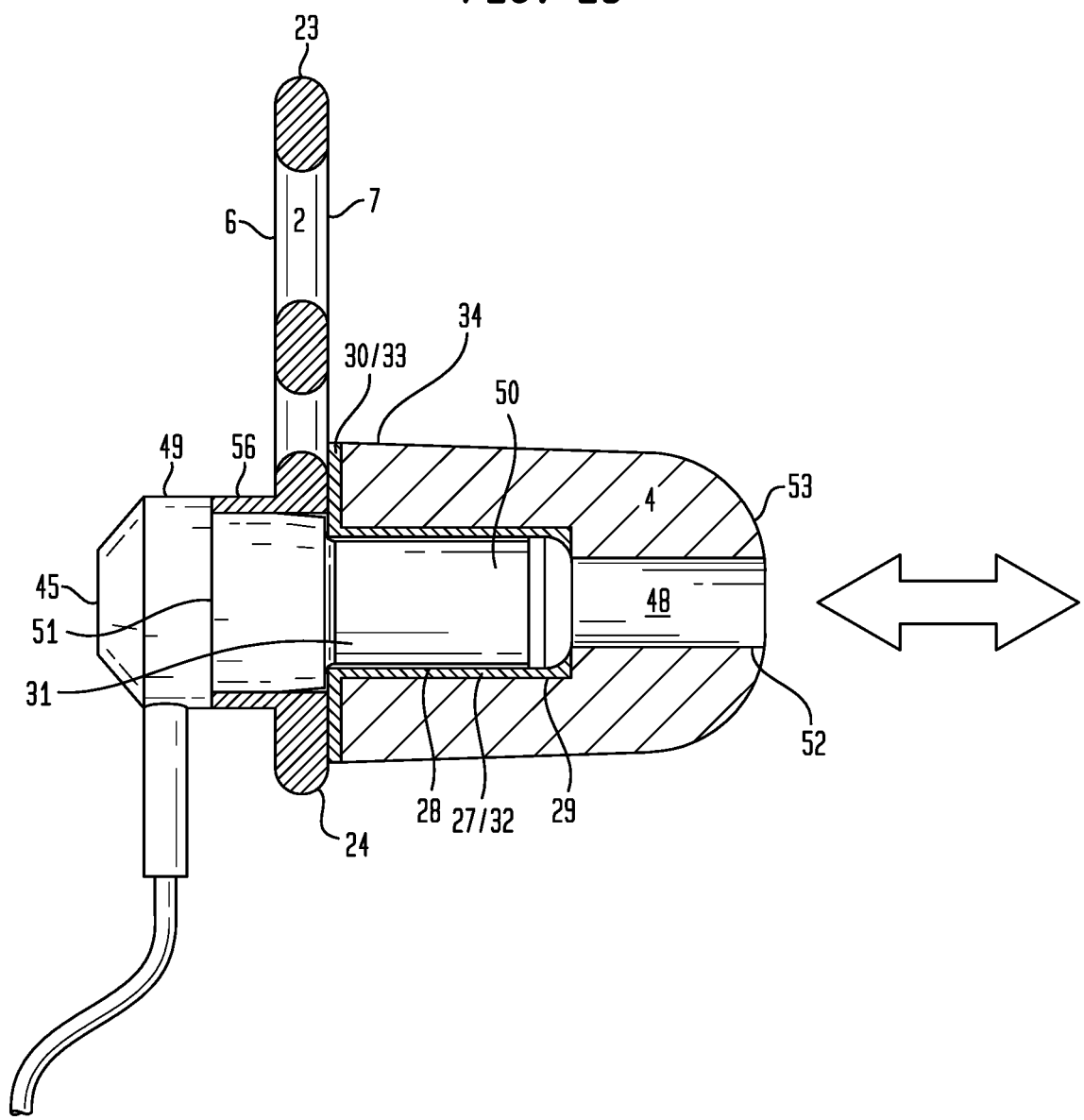

FIG. 26 is a cross sectional side view 26-26 of the particular embodiment of an intra-auricular support having the intra-auricular support conduit retaining an in-ear device with the sound delivery element extending outwardly from the intra-auricular support to provide the projection element, and the flexible body removably coupled to the projection element.

Figure 27:
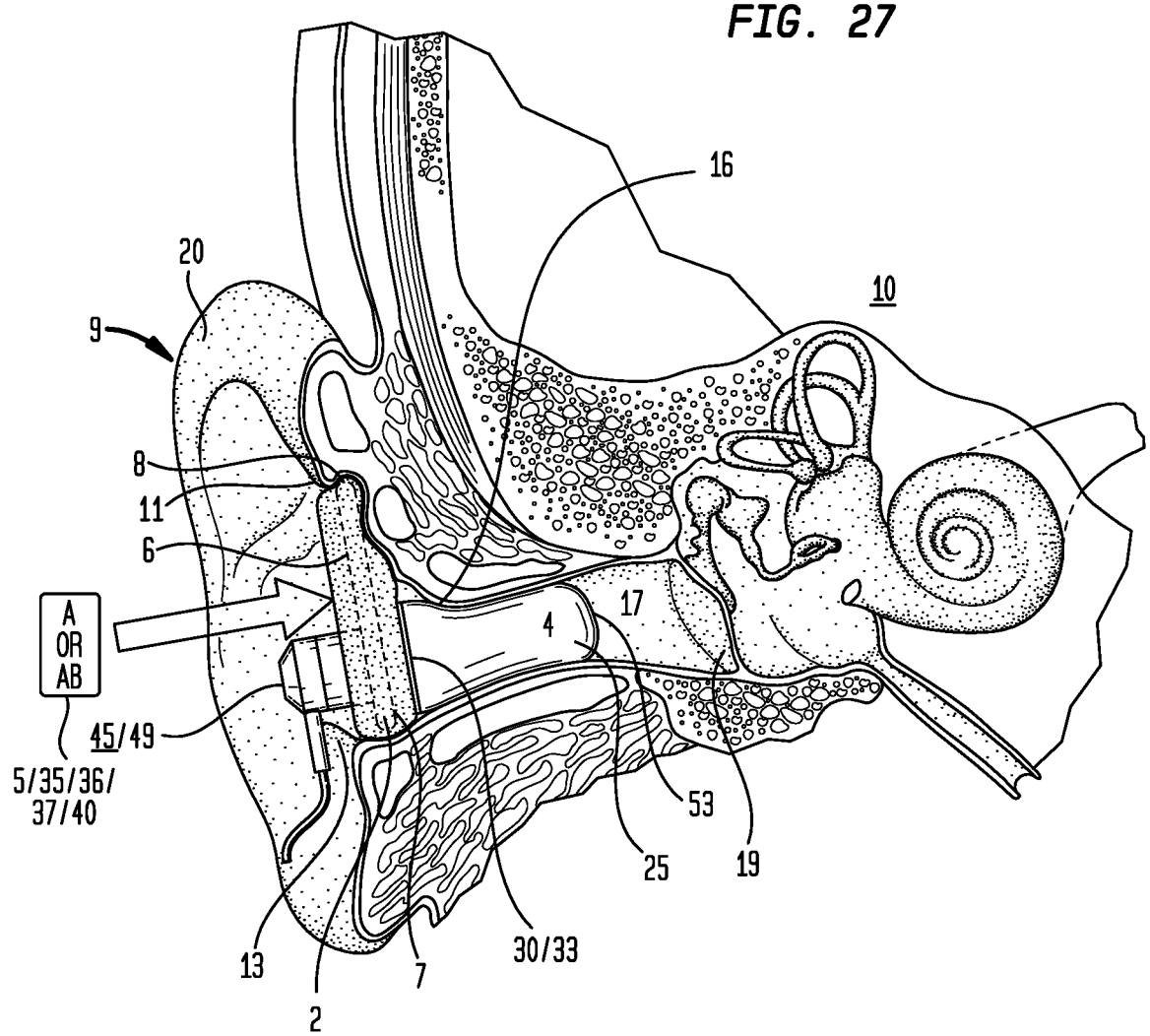

FIG. 27 is a cross sectional side view of the particular embodiment of the intra-auricular support having the intra-auricular support conduit retaining an in-ear device with the sound delivery element extending outwardly from the intra-auricular support to provide the projection element, and the flexible body engaged with the external ear canal of the ear and further illustrating a moldable earpiece material A or AB molded about the intra-auricular support and to the contour of the auricle of the ear to provide a fixed configuration of the earpiece.

Figure 28:
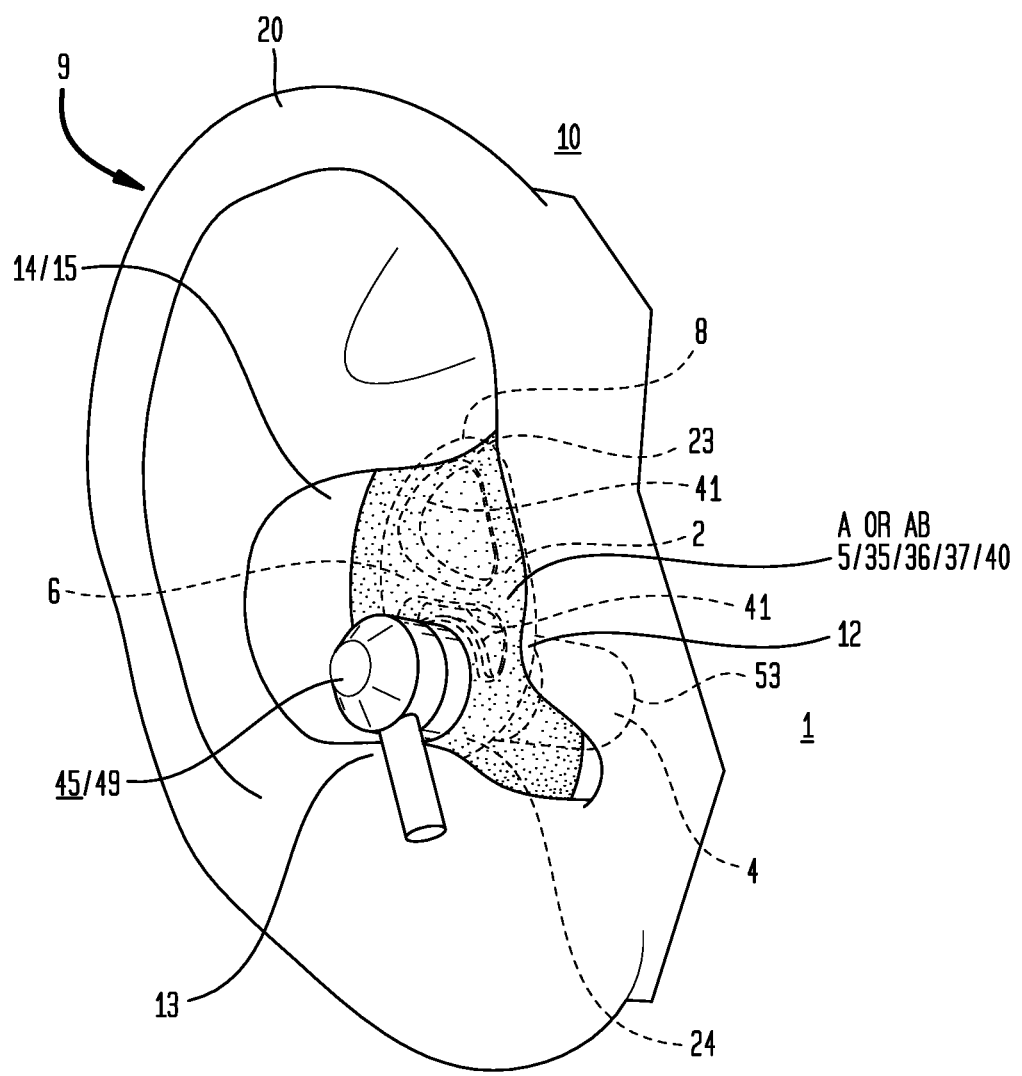

FIG. 28 is a perspective view of the particular embodiment of the fixed configuration of the earpiece in an ear.

Figure 29:
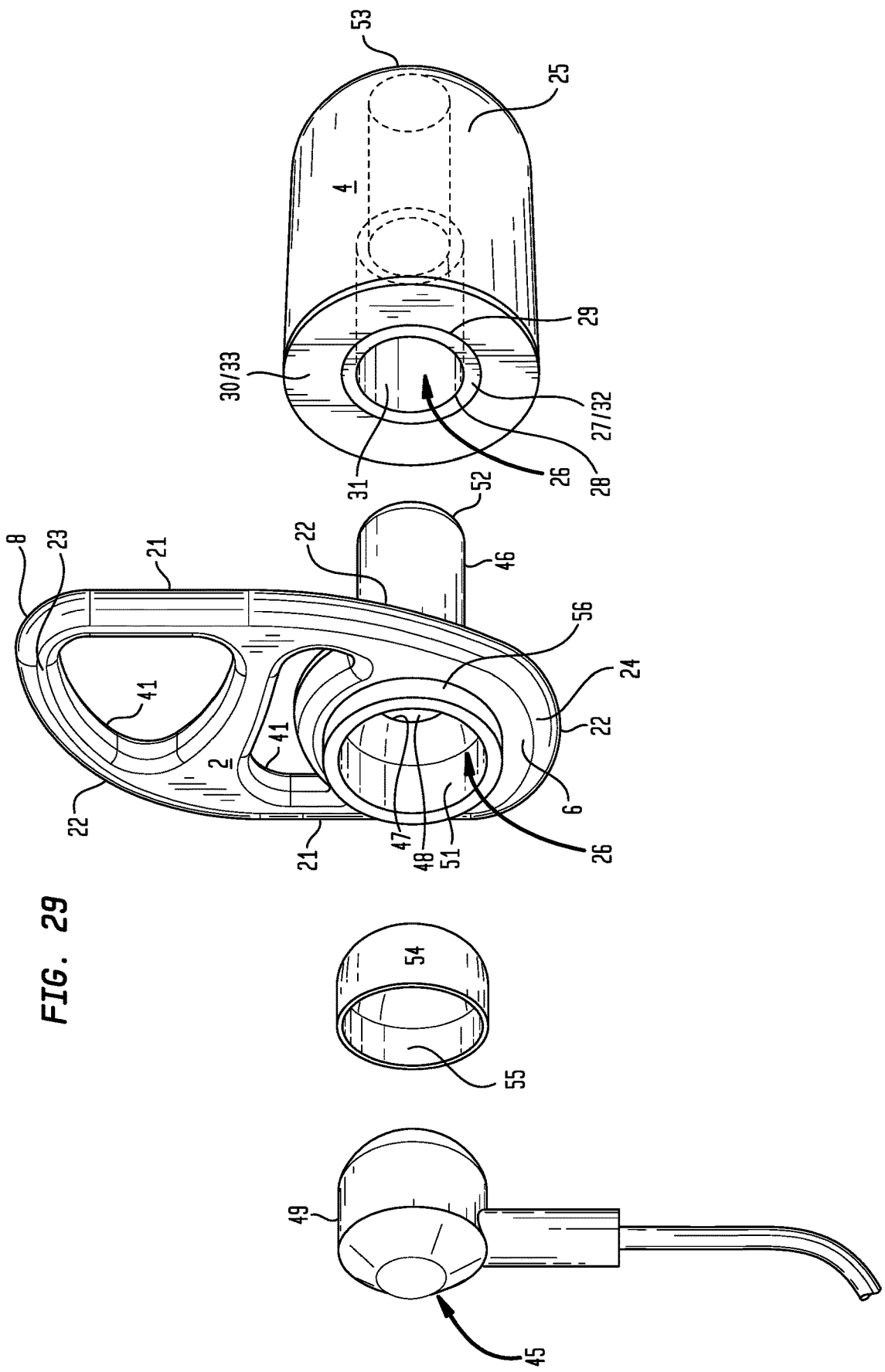

FIG. 29 is an exploded view of the particular embodiment of an intra-auricular support having an intra-auricular support conduit including a flexible elastomer insert configured to removably retain an in-ear device a projection element extending outward from the inner surface of the intra-auricular support, and a flexible body which removably couples to the projection element.

Figure 30:
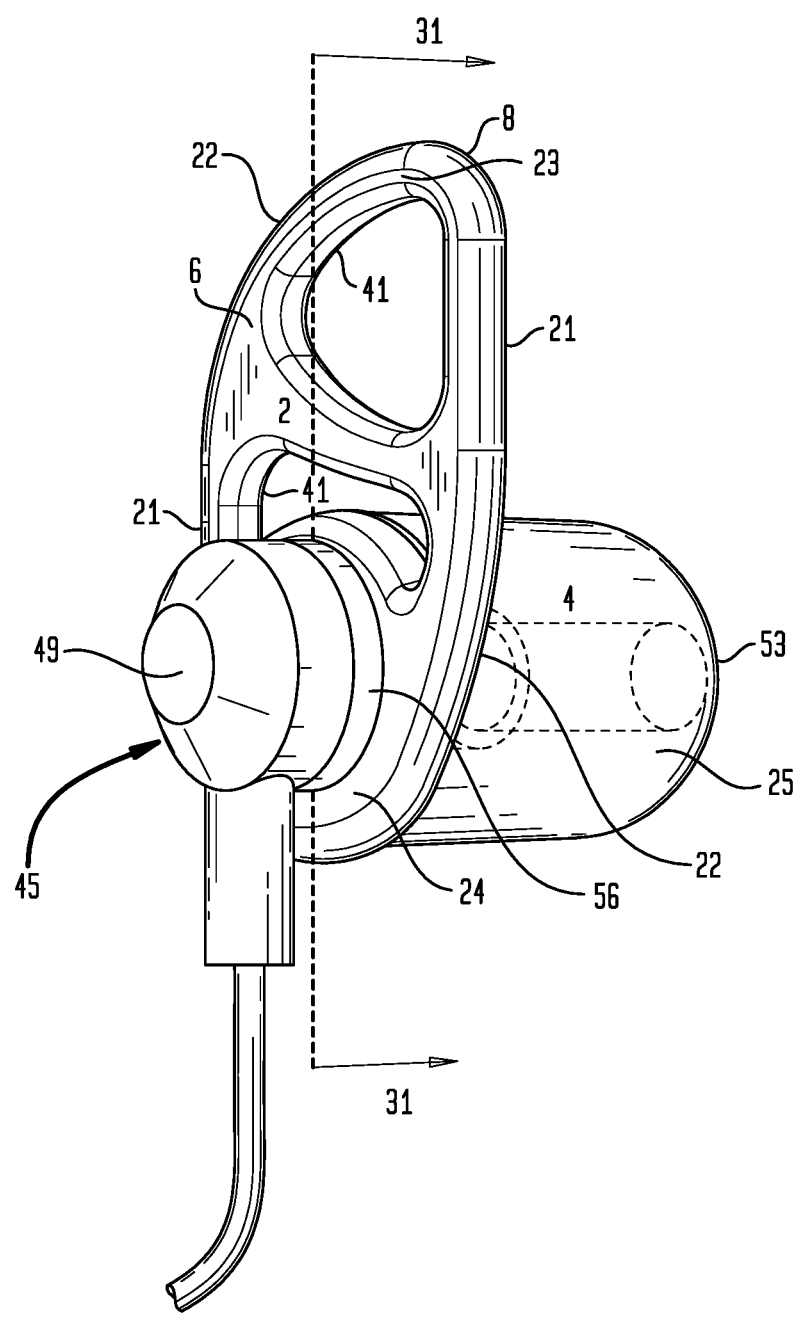

FIG. 30 is a perspective view of the particular embodiment of an intra-auricular support having an intra-auricular support conduit including a flexible elastomer insert removably retaining an in-ear device, a projection element extending outwardly from the intra-auricular support, and a flexible body removably coupled to the projection element.

Figure 31:
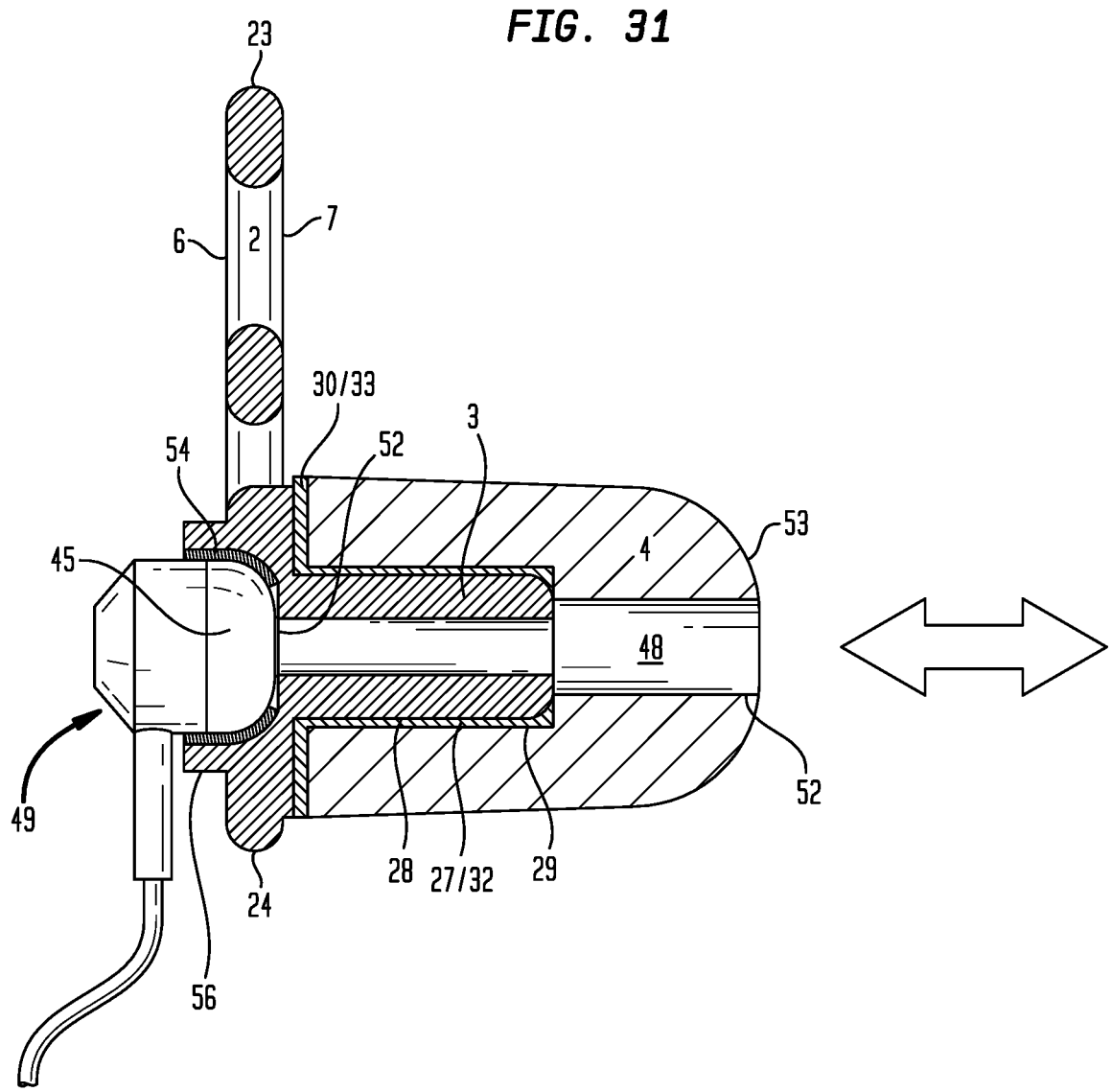

FIG. 31 is a cross sectional side view 31-31 of the particular embodiment of an intra-auricular support shown in FIG. 30 having the intra-auricular support conduit including a flexible elastomer insert retaining an in-ear device.

V. DETAILED DESCRIPTION OF THE PREFERRED EMBODIMENTS

Figure 7:
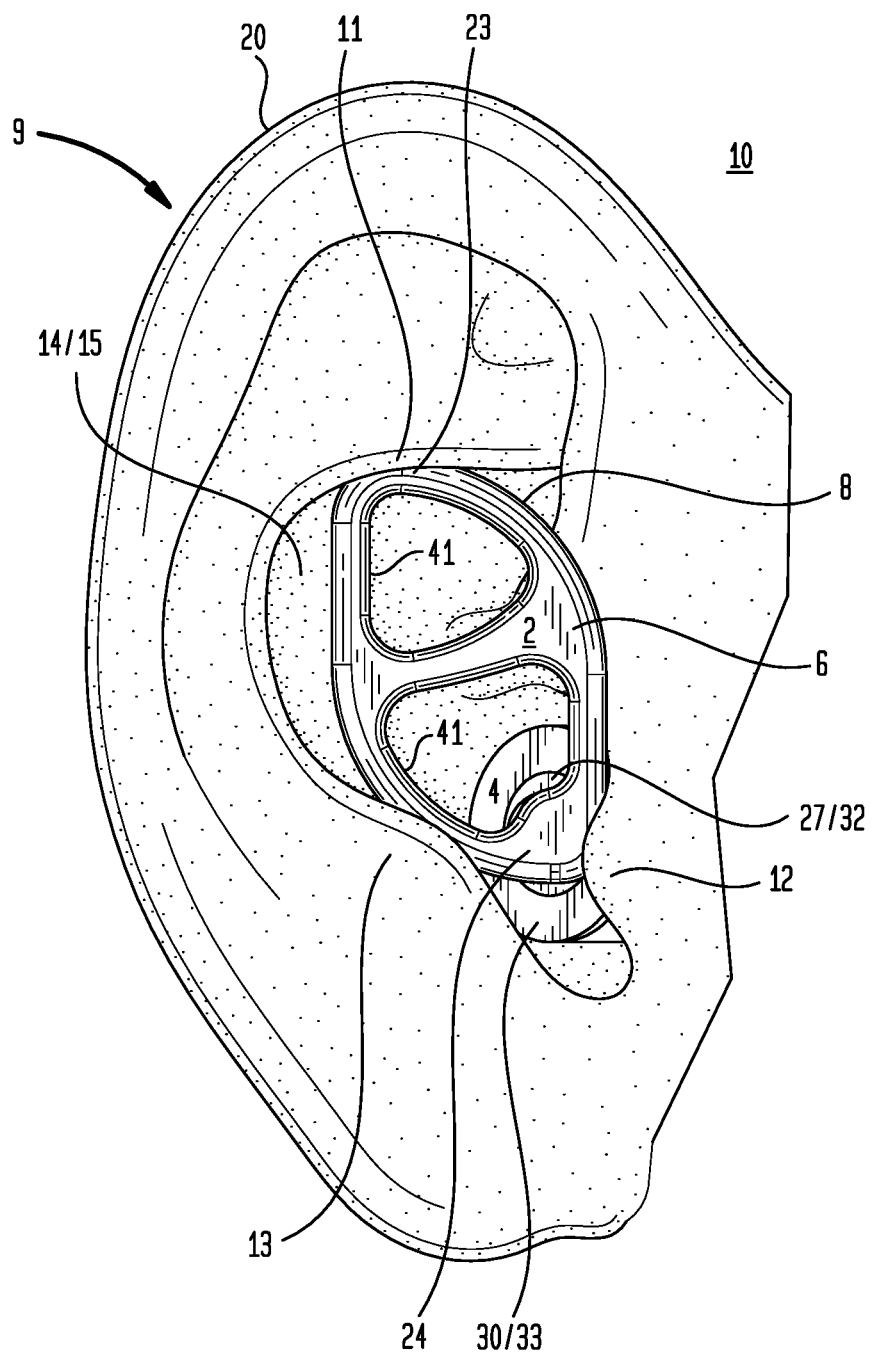
FIG. 7 is an illustration of the particular embodiment of an intra-auricular support, projection element, and flexible body having the intra-auricular support engaged with the auricle of the ear concurrent with the flexible body disposed in the external ear canal of an ear.

Generally referring to FIGS. 1 through 31, particular embodiments of an earpiece (1) can include one or more of:

an intra-auricular support (2), a projection element (3), a flexible body (4), and a moldable earpiece material (5). The intra-auricular support (2) can have an outer surface (6) opposite an inner surface (7), where each surface extends to an intra-auricular support peripheral edge (8). The intra-auricular support (2) extending to the intra-auricular support peripheral edge (8) can be configured to be positioned within an auricle (9) of the ear (10). As to particular embodiments, the intra-auricular support (2) can be positioned within the area of the auricle (9) of the ear (10) anatomically defined by the antihelix (11), tragus (12), antitragus (13), and concha (14), also referred to herein as the concha bowl (15), and concurrently defining an inner surface (7) of the intra-auricular support (2) of sufficient area which precludes ingress of the external ear canal opening (16)(as shown in the example of FIG. 7). For purposes of this invention the term "external ear canal (17)" means the portion of the ear canal (or auditory canal) communicating between the auricle (9) of the ear (10) and the tympanic membrane (19). For purposes of this invention, the term, "auricle (9)" means the area of the ear (10) outside of the external ear canal (17) including the concha bowl (15) and extending to the peripheral edge (20) of the ear (10)(also referred to as the "ear pinna").

Figure 3:
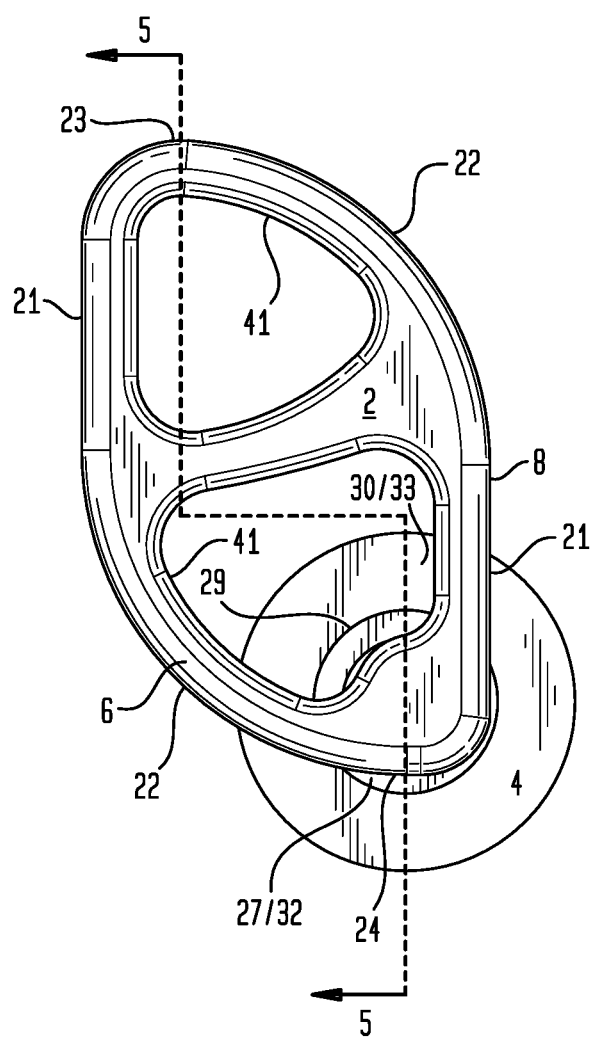
FIG. 3 is a front view of the particular embodiment of the intra-auricular support, the projection element, and the flexible body.

Now referring primarily to FIGS. 3 and 7, as to particular embodiments, the intra-auricular support (2) can be configured to be positioned in the concha bowl (15) concurrent with the flexible body (4) engaged with the external ear canal (17). While the intra-auricular support peripheral edge (8) of the embodiment shown in FIGS. 3 and 7 generally defines a quadrilateral having a pair of linear opposed sides (21) interconnected by a pair of arcuate sides (22), this example of the configuration of the intra-auricular support (2) is not intended to preclude other configurations of the intra-auricular support (2) in which the intra-auricular support peripheral edge (8) can generally define a circle, an ellipse, triangle, or other configuration disposable in the auricle (9) of the ear (10) and, more particularly, disposed within the concha bowl (15).

Figure 10:
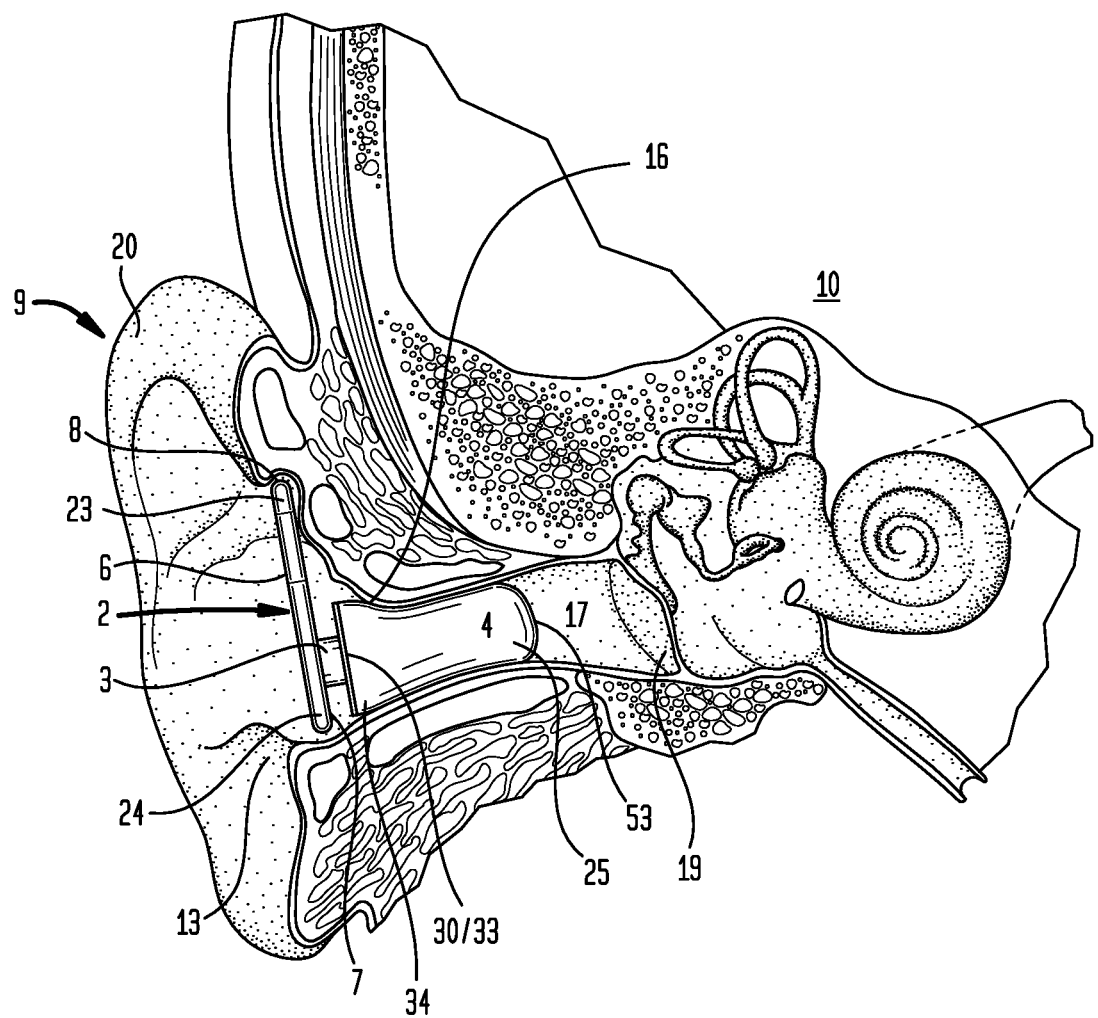
FIG. 10 is a cross sectional side view of an ear and the particular embodiment of an intra-auricular support, projection element, and flexible body which shows the intra-auricular support engaged with the auricle of the ear concurrent with the flexible body disposed in the external ear canal of an ear.

Now referring primarily to FIGS. 7 and 10, the intra-auricular support (2) can be configured to be disposed in the concha bowl (15) and retained in the concha bowl (15) by contact of the antihelix (11), antitragus (13), or tragus (12) with the corresponding portions of the intra-auricular support (2). As shown by the example of FIG. 7, a top portion (23) of the intra-auricular support peripheral edge (8) can be disposed behind the antihelix (11), and the lower portion (24) of the intra-auricular support peripheral edge (8) can be disposed behind the antitragus (13) and tragus (12).

Embodiments of the intra-auricular support (2) can fabricated, formed or molded from a wide variety of rigid or elastic thermoplastics including, but not necessarily limited to, acrylic, nylon, acrylonitrile butadiene styrene, polylactic acid, polybenzimidzole, polycarbonate, polyether sulfone, polyethylene, urethane, silicone, or combinations thereof.

Figure 4:
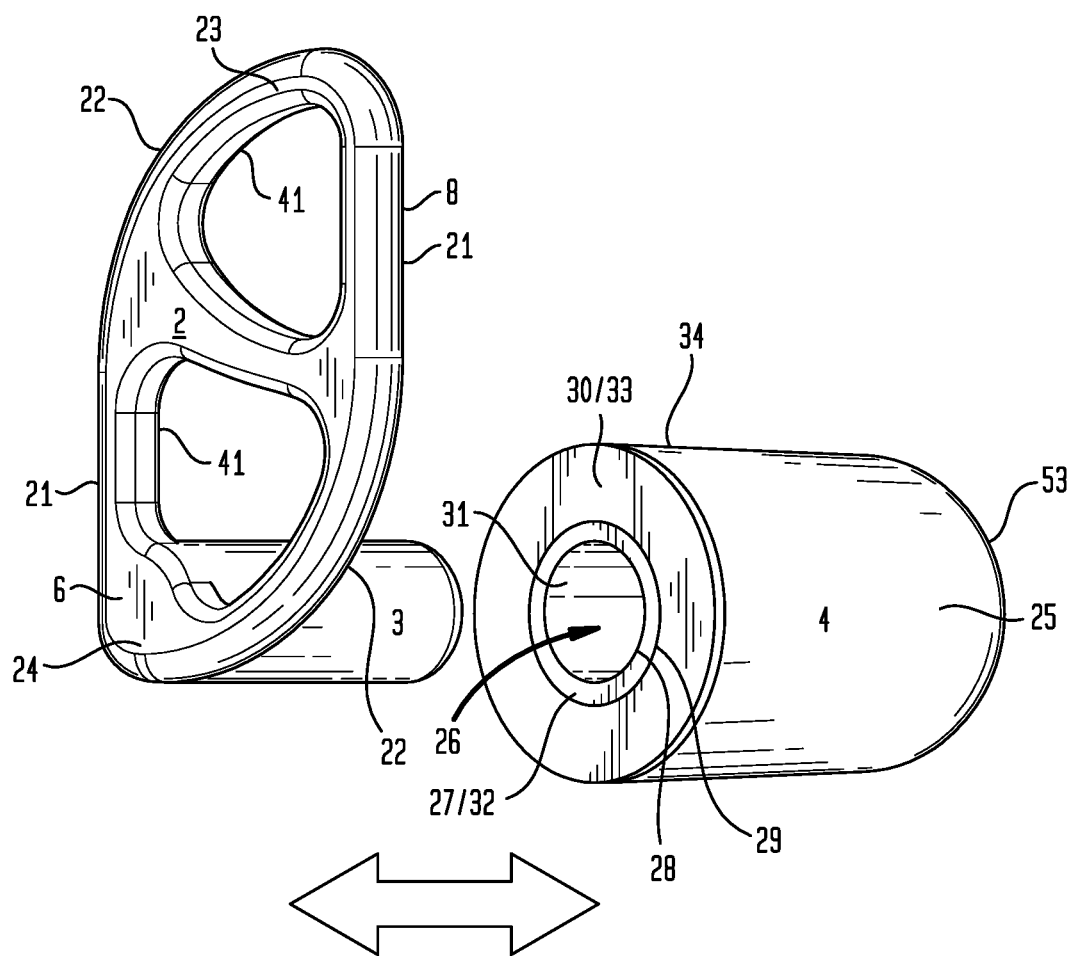
FIG. 4 is an exploded perspective view of the particular embodiment of an intra-auricular support, projection element, and flexible body.
Figure 5:
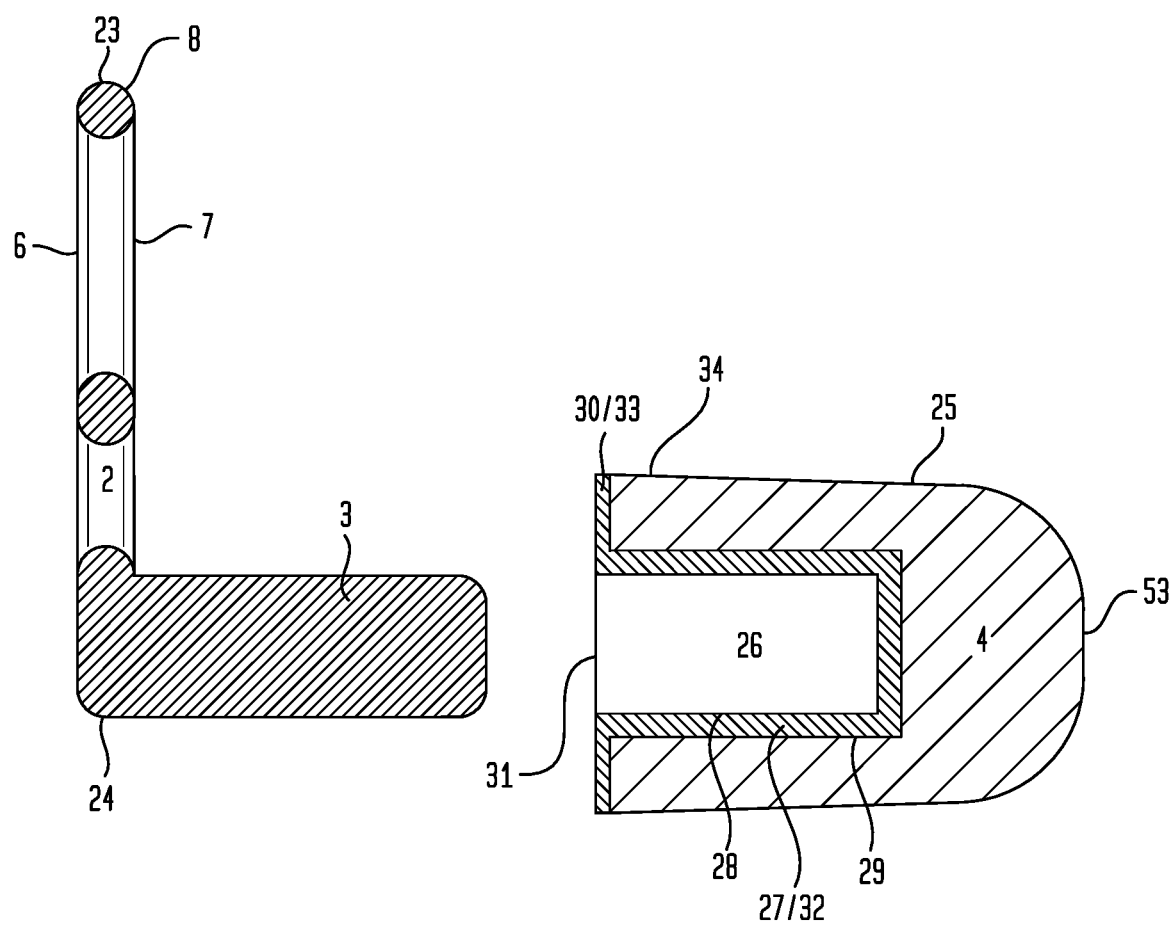
FIG. 5 is a cross sectional side view 5-5 of the particular embodiment of an intra-auricular support, projection element, and flexible body shown in FIG. 3.
Figure 6A:
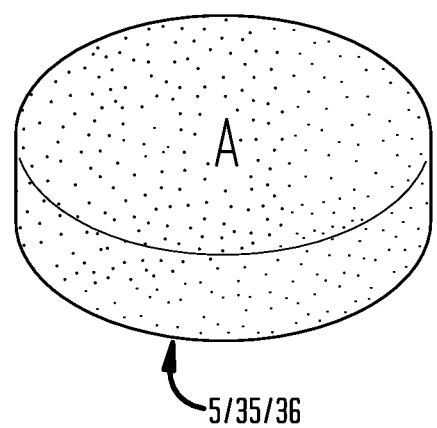
FIG. 6A is a particular embodiment of a one-part moldable earpiece material "A".
Figure 6B:
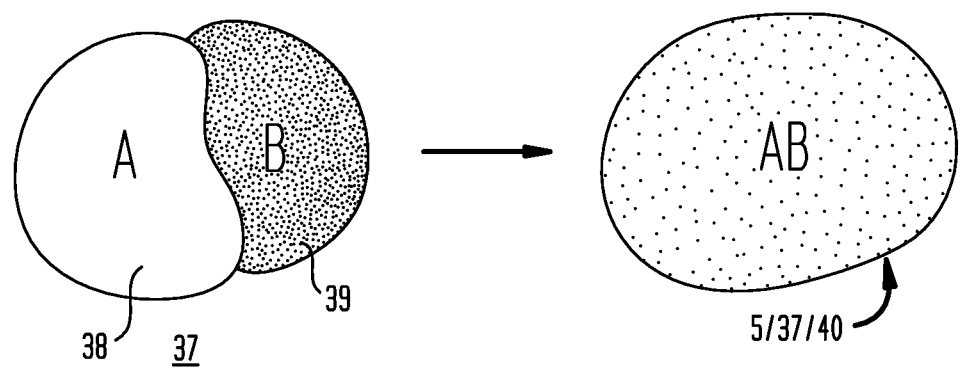
FIG. 6B is another particular embodiment of a moldable earpiece material including moldable agent "A" and a curing agent "B" combinable to generate moldable earpiece material "AB".

Now referring primarily to FIGS. 4 and 5, particular embodiments of the earpiece (1) can further include a projection element (3) outwardly extending from a location on the inner surface (7) of the intra-auricular support (2) which aligns the projection element (3) within the external ear canal (17) concurrent with the intra-auricular support (2) being disposed within the auricle (9) or concha bowl (15) of the ear (10). As to particular embodiments, the projection element (3) can be disposed on, coupled to, or directly coupled to the inner surface (7) of the intra-auricular support (2) at a location where the projection element (3) extends into the external ear canal (17) concurrent with the intra-auricular support (2) being disposed within the concha bowl (15) locating the inner surface (7) adjacent to the external ear canal opening (16). As exemplified in FIGS. 4 and 5, the location from which the projection element (3) can extend, the bottom portion of inner surface (7) of the intra-auricular support (2), can be proximate the intra-auricular support peripheral edge (8). The projection element (3) can be configured as a solid or tubular elongate member having circular, oval, square, rectangular, or cross sectional configuration otherwise disposable in the external ear canal (17).

The projection element (3) can comprise the same material(s) or different material(s) as the intra-auricular support (2), and as to particular embodiments, the intra-auricular support (2) and the projection element (3) can, but need not necessarily, be fabricated, formed or molded in one piece.

Again, referring generally to FIGS. 1 through 5 and FIGS. 10 through 31, particular embodiments of the earpiece (1) can, but need not necessarily, include a flexible body (4) disposed about the projection element (3). The flexible body (4) can be disposed inside of the external ear canal (17) of an ear (10) concurrent with the intra-auricular support (2) engaged within the auricle (9) or the concha bowl (15) with the inner surface (7) adjacent the external ear canal opening (16). Embodiments of the flexible body (4) can, but need not necessarily, comprise any one or a combination of pliant materials or bladders which deformably compress upon engagement with the external ear canal (17) and return toward the original configuration upon disengagement with surfaces of the external ear canal (17), such as foam, foam rubber, or hydrogel. As to particular embodiments, the flexible body (4) can further include a continuously smooth external surface (25).

Figure 1:
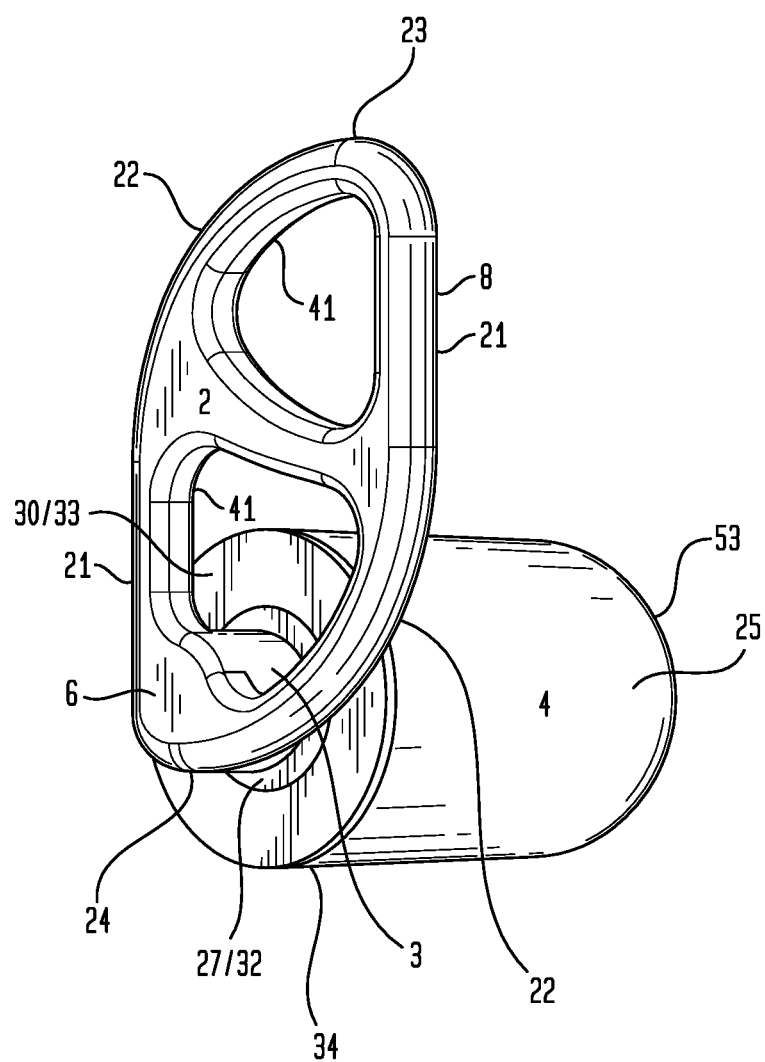
FIG. 1 is a perspective view of a particular embodiment of an intra-auricular support, a projection element coupled to the intra-auricular support, and a flexible body coupled about the projection element.
Figure 2:
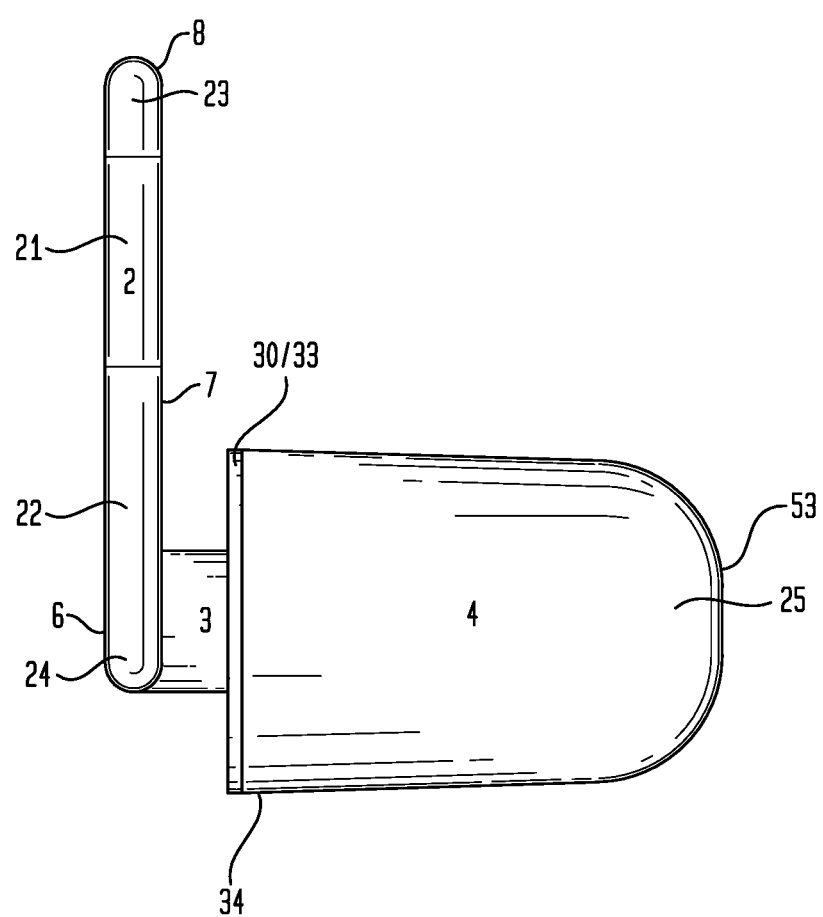
FIG. 2 is a side view of the particular embodiment of the intra-auricular support, the projection element, and the flexible body.

As to particular embodiments, the flexible body (4) can, but need not necessarily, be integrated with the projection element (3) as one piece or, as to other embodiments, removably coupled or connected to the projection element (3), as illustrated in the example of FIG. 4. In particular embodiments where the flexible body (4) removably couples to the projection element (3), the flexible body (4) can include a passage (26) disposed in the flexible body (4) and configured to accept the projection element (3). As illustrated in FIG. 5, the projection element (3) can be configured as a solid cylinder which can insertingly disposed in the flexible body passage (26) of the flexible body (4). As to particular embodiments, the flexible body (4) can further include a flexible body conduit (27) having a flexible body conduit internal surface (28) which defines the flexible body passage (26) and an external surface (29) which engages the flexible body (4). The flexible body conduit (27) can further include an annular flange (30) extending radially outward from the passage first end (31) toward the external surface (29) of the flexible body (4). As to particular embodiments, the flexible body conduit (27) and the annular flange (30) can comprise one piece. In other particular embodiments, as illustrated in FIGS. 1 and 3, the flexible body conduit (27) can, but need not necessarily, comprise two components where the first component (32) comprises the flexible body conduit (27) disposed within the passage (26) of the flexible body (4), and the second component (33) comprises the annular flange (30) coupled to the flexible body first end (34) and radially extending outward from the first component (32) disposed in the passage (26) toward the external surface (29) of the flexible body (4).

Now referring primarily to FIGS. 6A and 6B, and 11 through 13, 17, 18, 22, 23, 27 and 28, particular embodiments of the earpiece (1) can, but need not necessarily, further include a moldable earpiece material (5). The moldable earpiece material (5) can be molded about the intra-auricular support (2) to conform to the auricle (9) or the concha bowl (15) of the ear (10). The moldable earpiece material (5) can, but need not necessarily be, a single compound (35) (shown as compound "A" in FIG. 6A).

Figure 11:
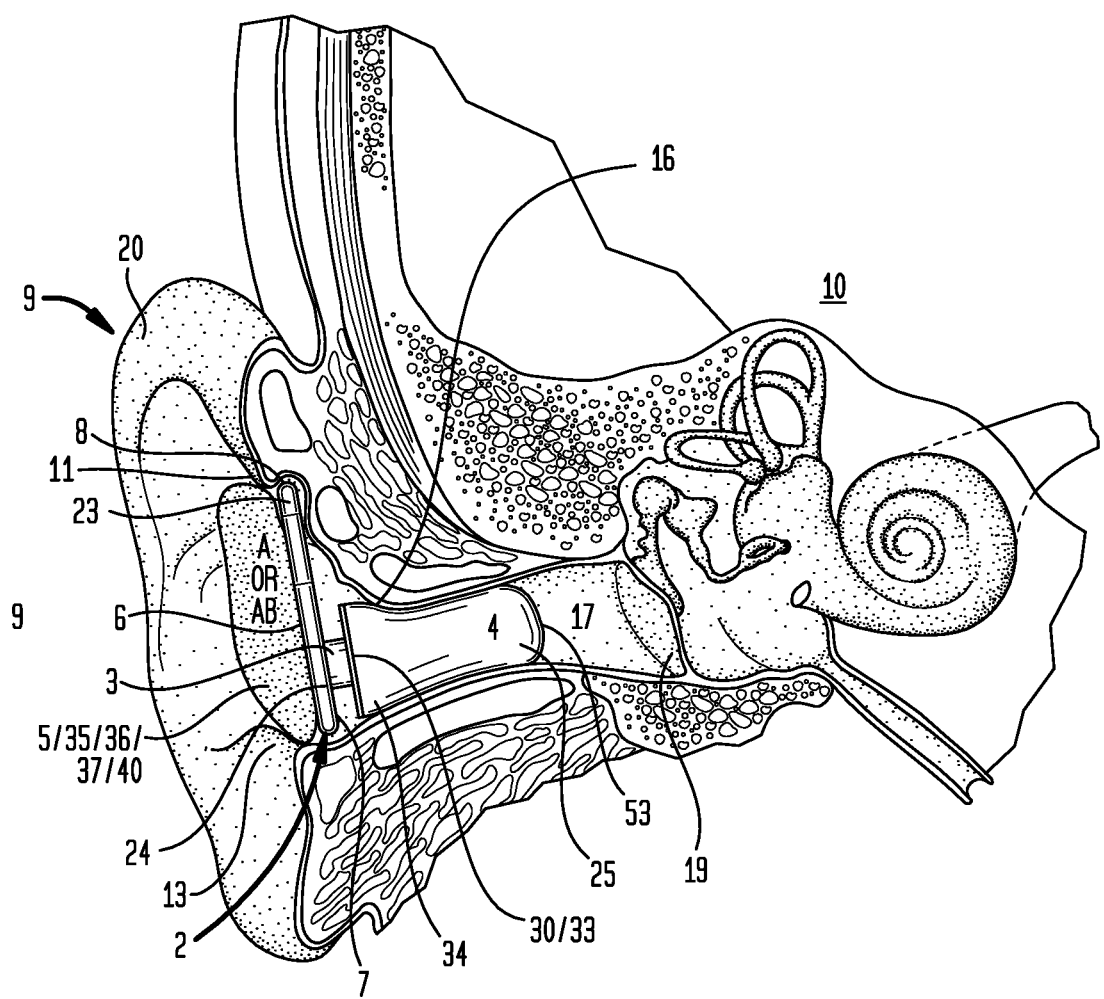
FIG. 11 is a cross sectional side view of the ear and the particular embodiment of an intra-auricular support, projection element, and flexible body engaged with the ear as shown in FIG. 10 and further illustrating a moldable earpiece material A or AB moldably engaged with the intra-auricular support and the auricle of the ear.
Figure 12:
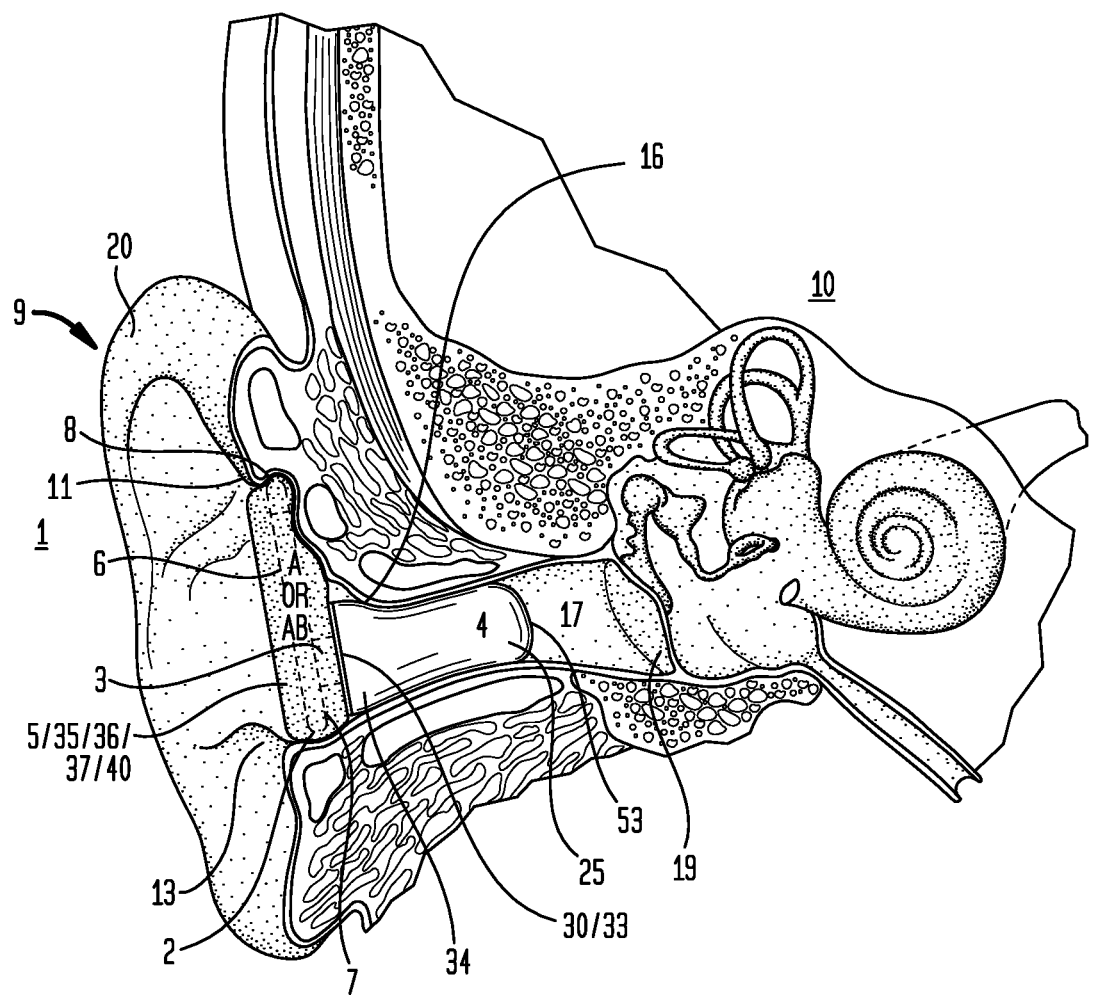
FIG. 12 is a cross sectional side view of the ear and the particular embodiment of an intra-auricular support, projection element, and flexible body engaged with the ear as shown in FIG. 11 and further illustrating a moldable earpiece material A or AB molded about the intra-auricular support and to the contour of the auricle of the ear to provide a fixed configuration of the earpiece.
Figure 13:
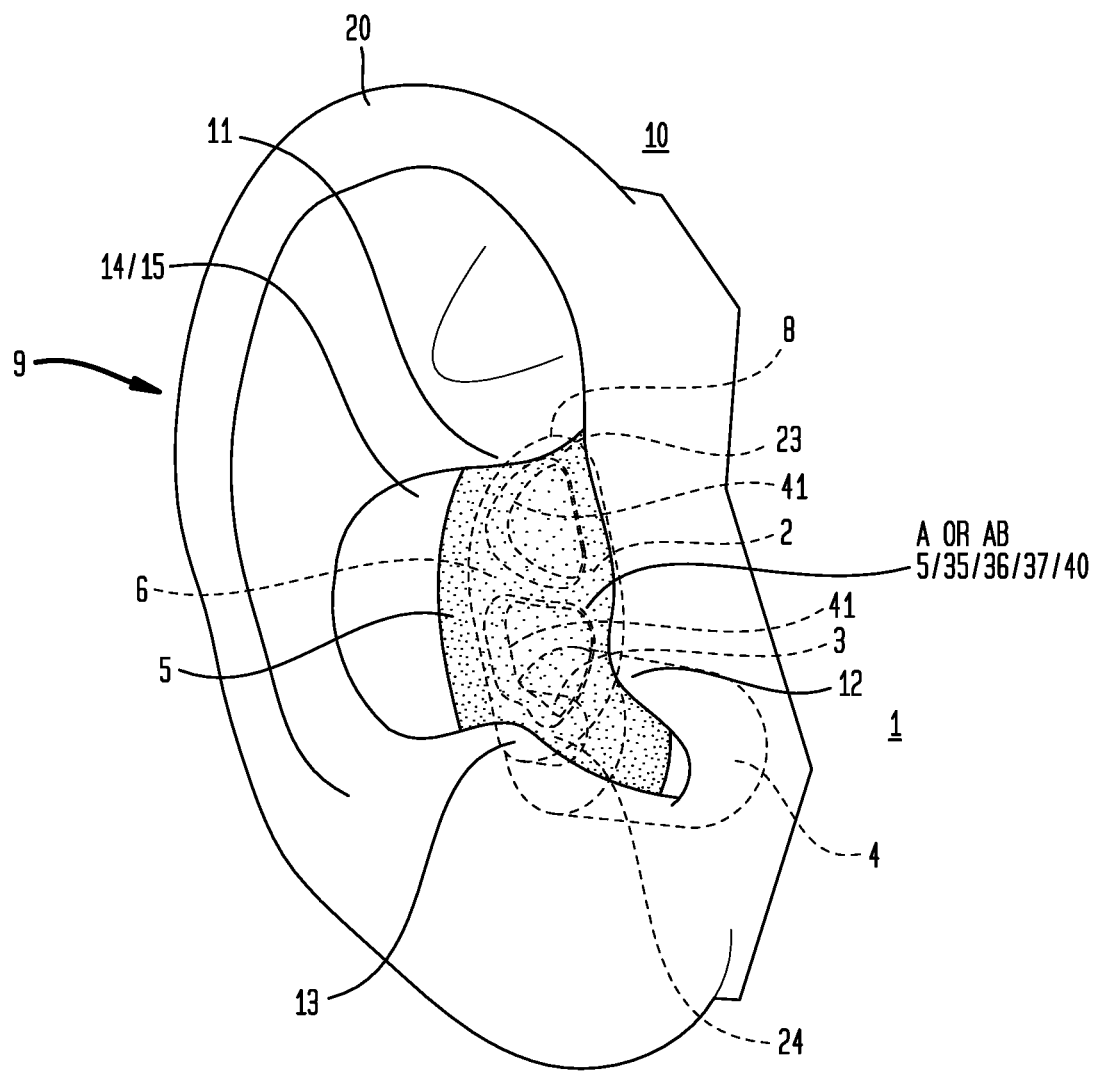
FIG. 13 is a perspective view of a particular embodiment of a fixed configuration of an earpiece in an ear.
Figure 14:
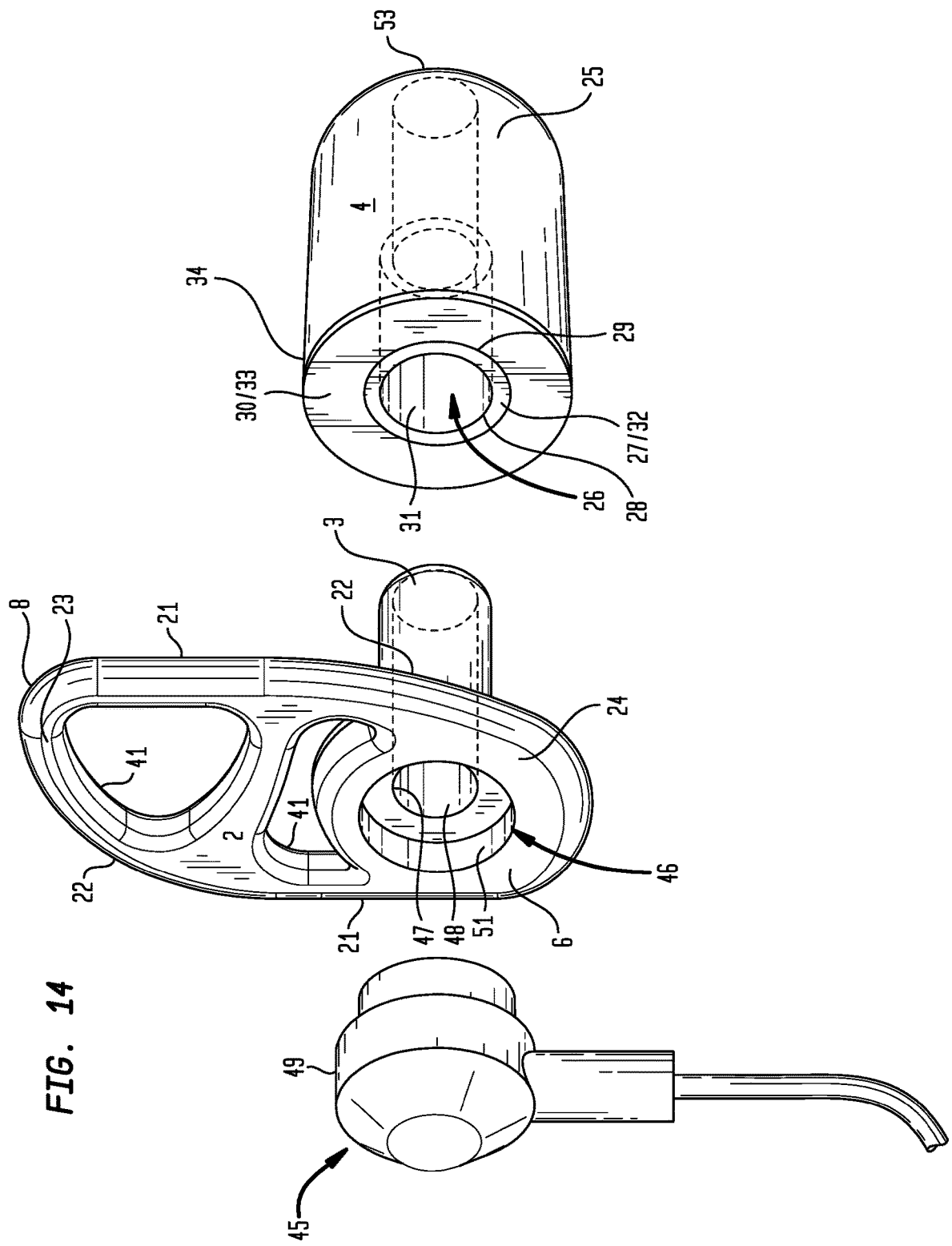
FIG. 14 is an exploded view of a particular embodiment of an intra-auricular support, a projection element outwardly extending from the intra-auricular support and a flexible body coupled about the projection element and an intra-auricular support conduit disposed in the intra-auricular support configured to removably retain an in-ear device.
Figure 15:
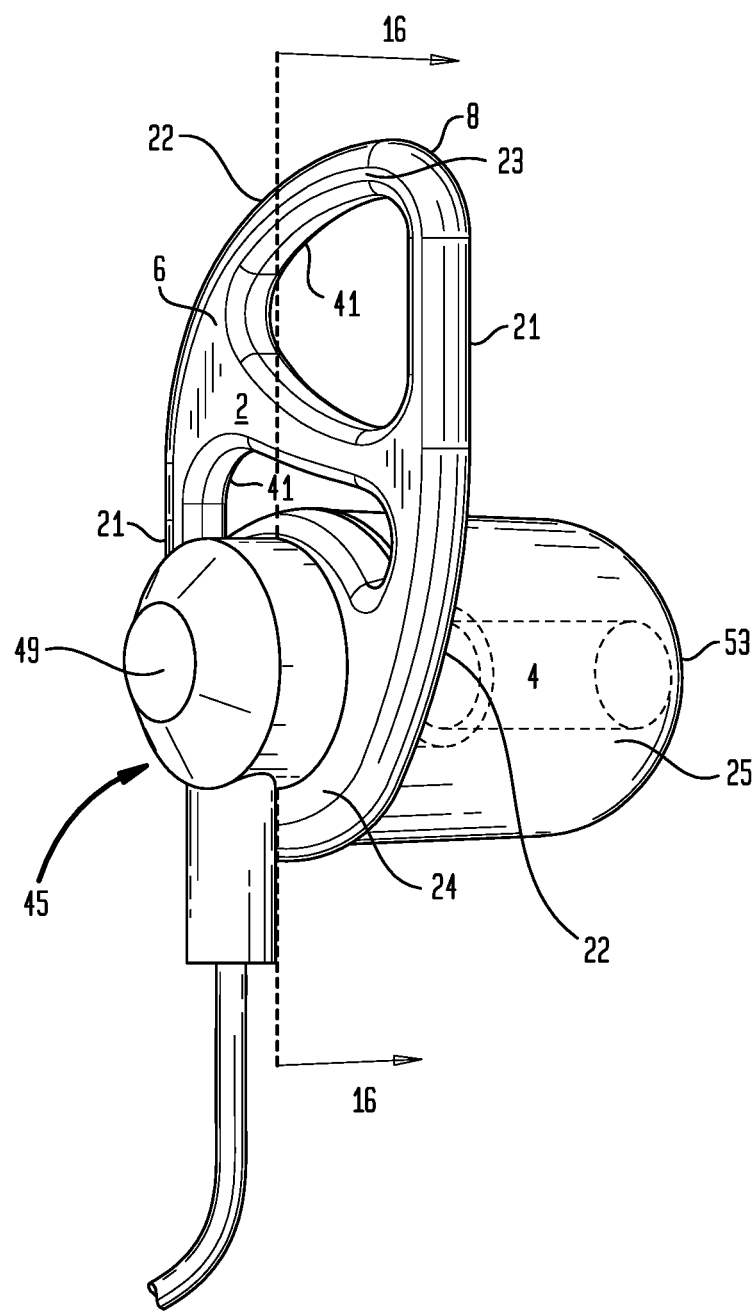
FIG. 15 is a perspective view of the particular embodiment shown in FIG. 14 including the intra-auricular support, the projection element, the flexible body, and the intra-auricular support conduit removably retaining an in-ear device.
Figure 16:
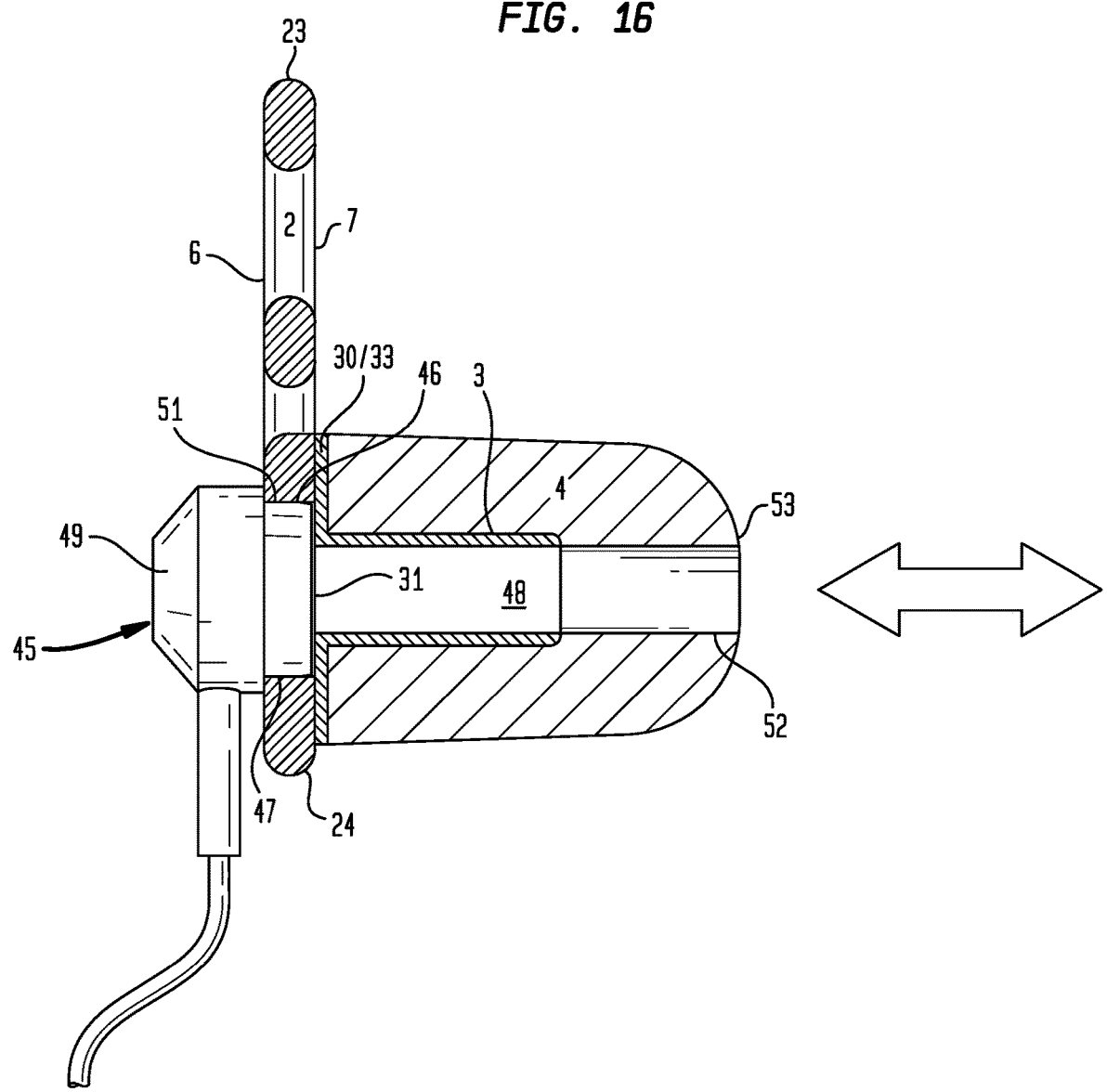
FIG. 16 is a cross sectional side view 16-16 of the particular embodiment of the intra-auricular support having the intra-auricular support conduit removably retaining an in-ear device, the projection element, the flexible body.

As to other embodiments, the moldable earpiece material (5) can, but need not necessarily, comprise a two-part moldable earpiece material (37) including or consisting of a moldable agent (38) (shown as compound "A" in FIG. 6B) combinable with a curing agent (39) (shown as compound "B" in FIG. 6B) which can be mixed together prior to molding to form a single mixed compound (40) (shown as compound "AB" in FIG. 6B) capable of being moldable about, coupled to, or adhering to the intra-auricular support (2) by forcibly urging the single mixed compound (40) onto or about the intra-auricular support (2) (as shown in the example of FIGS. 11 and 12, 17 and 18, 22 and 23, and 27 and 28). Concurrently, the moldable earpiece material (5), whether a one-part moldable earpiece material (36) or a two-part moldable earpiece material (37) to provide a single mixed compound (40), can be molded to the contour of the auricle (9) or the concha bowl (15) of the ear (10) (as shown in the example of FIGS. 12 and 13, 17 and 18, and 22 and 23). After molding about the intra-auricular support (2), the single compound (35) or single mixed compound (40) can then cure over a period of time at ambient temperature (or at a temperature greater or lesser than ambient temperature) to provide a fixed configuration of the moldable earpiece material (5)(as shown in the examples of FIGS. 13, 18, and 23).

In embodiments including a moldable earpiece material (5) comprising or consisting of a single compound (35), the single compound (35) can include or consist of one or more of: ethyl vinyl acetate, polycaprolactone, silicone, or like thermoplastic materials. Single compound (35) moldable earpiece materials (5) transition from a moldable condition to the fixed condition by exposure to external factors such as moisture, temperature, or ultraviolet light.

As one illustrative example, the single compound (35) can be an amount of polycaprolactone polymer (CAS No.: 24989-40-4) having the properties described in Table 1; however, this illustrative example is not intended to preclude the use of other thermoplastic polymers suitable for use with embodiments of the earpiece (1).

TABLE 1

Physical Properties of Polycaprolactone Thermoplastic Polymers

| Physical Property | ASTM Test | | |
|---|---|---|---|
| Molecular Weight | | | |
| Mn | GPC, THF, 25° C | 37,000 ± 2000; 47500 ± 2000; | 69000 ± 1500 |
| Mw | GPC, THF, 25° C. | 84500 ± 1000; | 120000 ± 2000 |
| Mz | GPC, THF, 25° C. | 130000 ± 5000; | 178500 |
| Polydispersity (Mw/Mn) | | 1.78 | 1.74 |
| Melt Flow Index | D 1238 | | |
| 80° C., 2.16 kg, g/10 min | | 2.36 | 0.59 |
| 80° C., 21.6 kg, g/10 min | | 34.6 | 9.56 |
| 190° C., 2.16 kg, g/10 min | | 28 | 7.29 |
| Thermal Analysis (DSC) | | | |
| Melting Point ° C. | | 60-62 | 60-62 |
| Heat Of Fusion, DHm, J/g | | 76.9 | 76.6 |

TABLE 1-continued

Physical Properties of Polycaprolactone Thermoplastic Polymers

| Physical Property | ASTM Test | | |
|---|---|---|---|
| Crystallinity, % | | 56 | 56 |
| Crystallisation Temperature, ° C. | | 25.2 | 27.4 |
| Glass Transition Temperature, Tg, ° C. | | −60 | −60 |
| Tensile Properties | | | |
| Yield Stress, s y, Mpa | D 412-87 | | |
| 100 mm/min | | 17.5 | 16 |
| 500 mm/min | | 17.2 | 14 |
| Modulus , E. Mpa | D 412-87 | | |
| 1 mm/min | | 470 | 440 |
| 10 mm/min | | 430 | 500 |
| Draw Stress, s d, MPa | D 412-87 | | |
| 100 mm/min | | 12.6 | 11.9 |
| 500 mm/min | | 11.5 | 11 |
| Draw Ratio, 1 d, x | D 412-87 | | |
| 100 mm/min | | >4.2 | 4 |
| Stress At Break, s b, Mpa | D 412-87 | | |
| 100 mm/min | | 29 | 54 |
| Strain At Break, e b, % | D 412-87 | | |
| 100 mm/min | | >700 | 920 |
| Flexural Modulus, E, MPa | D 790 | | |
| 2 mm/min | | 411 | nd |
| Hardness | D 2240 | | |
| Shore A | | 95 | 94 |
| Shore D | | 51 | 50 |
| Viscosity | | | |
| Pa. sec, 70° C., 10 1/sec | | 2890 | 12650 |
| Pa. sec, 100° C., 10 1/sec | | 1353 | 5780 |
| Pa. sec, 150° C., 10 1/sec | | 443 | 1925 |

Polycaprolactone polymers can be heated to achieve a moldable condition, molded about the intra-auricular support (2), and contoured to the configuration of the auricle (9) or concha bowl (15) and cooled to achieve the fixed configuration of the earpiece (1).

Polycaprolactone polymers impart good water, oil, solvent, and chlorine resistance. Polycaprolactone polymers are also compatible with a wide range of other materials (collectively referred to as "admixed agents"), such as: starch, to impart greater biodegradability; colorants, such as alcohol dyes or acrylic coloring agents; powders, such as acrylic powder; particulates of plastic, copolymer plastics, metal, bismuth oxychloride, or glitter, or the like, either separately or in various combinations. Polycaprolactone polymers are non-toxic and approved by the United States Food and Drug Administration for specific applications in the human body.

In embodiments including a moldable earpiece material (5) comprising or consisting of a single mixed compound (40), the single mixed compound (40) can include a cross-linkable polymer (compound "A") having at least one hydrolysable silane group, selected from the group including or consisting of: silane-modified polyoxyalkylenes, polyolefins, poly(meth)acrylates, polyurethanes, polyamides, and polysiloxanes; silicone putty partially hydrolyzed alkyl silicate, or combinations thereof, and a catalyst (compound "B") including: a metallic salt of an organic carboxylic acid catalyst in which the metal comprises or consists of one or more of a platinum, tin, copper, or other metal.

One illustrative example of a single mixed compound (40) including a moldable agent (38) and curing agent (39) comprises polydimethylsiloxane polymer and platinum (0)-1,3-divinyl-1,1,3,3-tetramethyldisiloxane curing agent (39). Another illustrative example of a single mixed compound (40) including a moldable agent (38) and curing agent (39)

comprises two proprietary compounds manufactured by Radians, Inc., silicone putty A-side and silicone putty B-side, of which one silicone putty contains methylpolysiloxanes.

Yet another illustrative example includes SILPURAN® 8020, a platinum catalyst-curing solid silicone rubber available through Wacker Chemie AG.

TABLE 2

Physical Properties of SILPURAN ® 8020

| | |
|---|---|
| Hardness-Shore A (DIN 54615) | 62 |
| Cure System | Platinum (100:1.5 Base + catalyst) |
| Specific Gravity (DIN 54589 A) | 1.16 g/cm$^3$ |
| Tensile Strength (DIN 54614S1) | 10.5 N/mm$^2$ |
| Elongation at break (DIN54614S1) | 751% |
| Rebound Resilience (DIN54622) | 58% |
| Tear Resistance (ASTM D624B) | 30 N/mm$^2$ |
| Comprssion set (22 h/175° C.) (DIN ISO815-B) | 30% |
| Appearance-Translucent | |

Now generally referring to FIGS. 1 through 31, embodiments of the intra-auricular support (2) can, but need not necessarily, include one or more aperture elements (41) which communicate between the outer surface (6) and the inner surface (7) of the intra-auricular support (2). As shown in the examples of FIGS. 11 and 12, the moldable earpiece material (5) can pass through the aperture elements (41) to envelop both the outer surface (6) and inner surface (7) of the intra-auricular support (2) and further allow the moldable earpiece material (5) to conform to the auricle (9) or concha bowl (15) of the ear (10). Additionally, by engaging the moldable earpiece material (5) with the one or more aperture elements (41), a greater surface area of the intra-auricular support (2) can be integrated with the moldable earpiece material (5) than if the moldable earpiece material (5) only engaged the outer surface (6), thereby making the cured moldable earpiece material (5) less likely to separate in whole or in part from the intra-auricular support (2).

Figure 8:
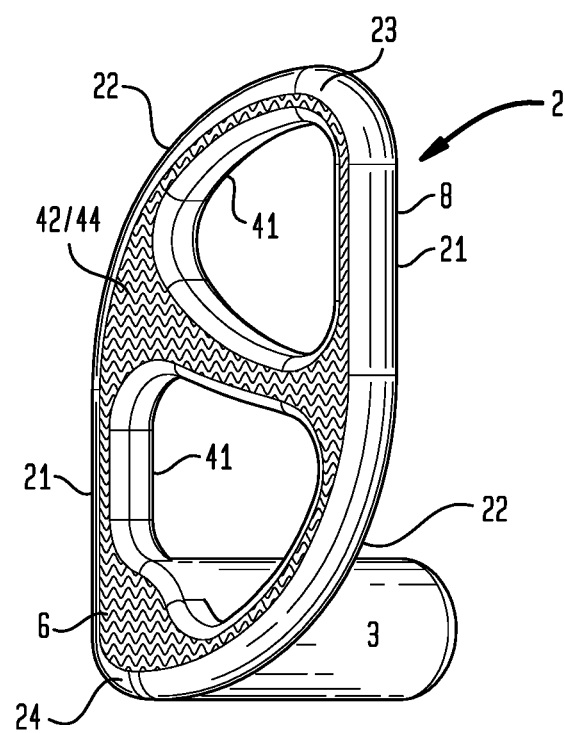
FIG. 8 is a particular embodiment of the intra-auricular support having patterned surface elements as an adhesion element.

Now referring primarily to FIG. 8, embodiments of the intra-auricular support (2) can, but need not necessarily, include adhesion elements (42). As to particular embodiments, the adhesion elements (42) can be configured as patterned surface elements (44) disposed on or in the outer surface (6) or inner surface (7) of the intra-articular support (2). The patterned surface elements (44) can provide an irregular or uniform pattern, texture, or roughness sufficient to fix or reduce travel of the moldable earpiece material (5) on or about the intra-auricular support (2). As to certain embodiments, the patterned surface elements (44) can provide recesses disposed in the intra-auricular support (2), which can function to sequester the moldable earpiece material (5) (as shown in FIG. 8), or provide protuberances that extend outward of the intra-auricular support (2) to penetrate the moldable earpiece material (5), or combinations thereof. The patterned surface elements (44) can be one piece with the intra-auricular support (2) or can be applied to the intra-auricular support (2) as a layer or individual elements.

Figure 9A:
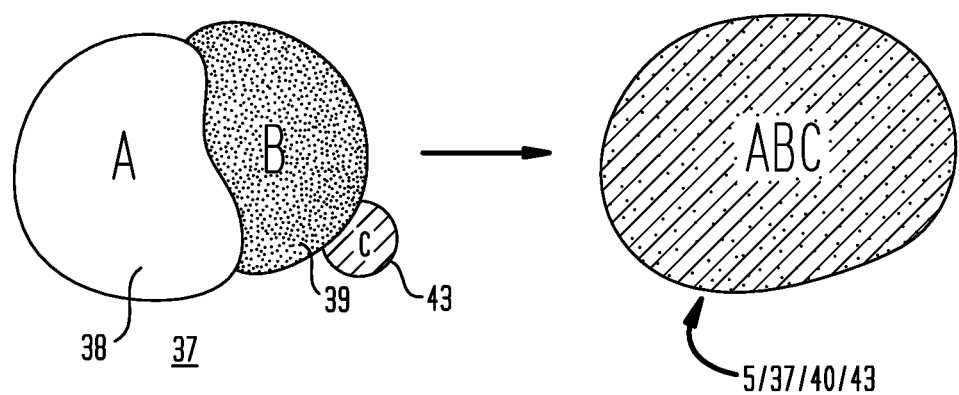
FIG. 9A is a particular embodiment of a moldable earpiece material including a tackifier "C" as an adhesion element.
Figure 9B:
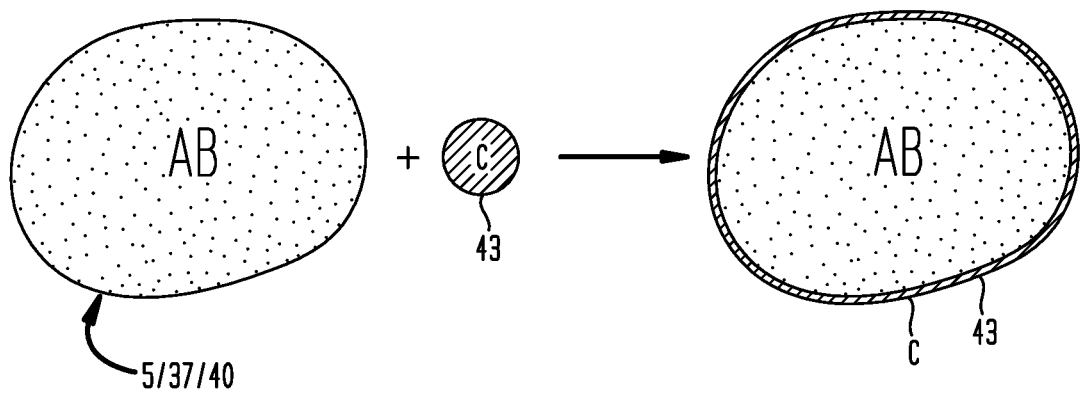
FIG. 9B is another particular embodiment of a moldable earpiece material having a tackifier "C" as an adhesion element.

Now referring primarily to FIGS. 9A and 9B, as to particular embodiments of the intra-auricular support (2), the adhesion elements (42) can comprise a tackifier (43) (shown in FIGS. 9A and 9B as compound "C") incorporated into the moldable earpiece material (5) or applied to the inner surface (7) or the outer surface (6) of the intra-auricular support (2) to increase the tack, or stickiness, of the moldable earpiece material (5) or intra-auricular support (2).

As illustrative examples, the tackifier (43) can include or consist of one or more of rosin resins, hydrocarbon resins, terpene resins, or other like materials.

Now referring generally to FIGS. 14 through 31, particular embodiments of the earpiece (1) can be provided separate from, but capable of use with, one or more of a wide variety of in-ear devices (45), for example: earphones, earplugs, earbuds, sealing balloons, ear tips, ear tubes, ear speakers, and in-ear hearing aids, or the like. As to particular embodiments, the in-ear devices (45) can be a part of an apparatus worn or which resides outside of the ear (10), for example: headsets, head phones, telephones, BLUETOOTH® headphones, wireless headphones, hearing aids, medical apparatus, or the like.

Particular embodiments of the earpiece (1) capable of use with an in-ear device (45) can include an intra-auricular support conduit (46) communicating between the outer surface (6) of the intra-auricular support (2) and the inner surface (7) of the intra-auricular support (2). The intra-auricular support conduit (46) can have an intra-auricular support conduit internal surface (47) configured to retain or releasably retain the in-ear device (45) in the earpiece (1) and which defines an intra-auricular support passage (48). The configuration of the intra-auricular support conduit internal surface (47) of the intra-auricular support conduit (46) can vary between embodiments to retain or releasably retain a wide variety of configurations of the in-ear device (45) including those configurations of the in-ear device (45) having a body (49) and a sound delivery element (50) which extends outward of the body (49) (as shown in the examples of FIGS. 19 through 28), or those configurations of the in-ear device (45) having a body (49) without a sound delivery element (50) which extends outward of the body (49) (as shown in the examples of FIGS. 14 through 18 and 29 through 31).

Now referring primarily to FIGS. 14 through 18, as to particular embodiments useful with in-ear devices (45) without an extended sound delivery element (50), the intra-auricular support (2) can include an intra-auricular support conduit (46) having an intra-auricular support conduit internal surface (47) communicating between an intra-auricular support conduit first end (51) open at the outer surface (6) of the intra-auricular support (2) and an intra-auricular support conduit second end (52) open at the flexible body second end (53) and defining an intra-auricular support passage (48). The intra-auricular support conduit (46) can be configured proximate the intra-auricular support conduit first end (51) to releasably retain the in-ear device (45). The configuration of the intra-auricular support conduit internal surface (47) can vary between embodiments to retain or releasably retain a wide variety of configurations of the in-ear device (45). The intra-auricular support conduit passage (48) communicates from the outer surface (6) of the intra-auricular support (2) to the inner surface (7) of the intra-auricular support (2), through the projection element (3), and through the flexible body (4) to the flexible body second end (53) for the transmission of sound from the in-ear device (45) releasably retained at the intra-auricular support conduit first end (51) to the flexible body second end (53).

Now referring generally to FIGS. 19 through 28, as to particular embodiments useful with in-ear device (45) including a sound delivery element (50) which projects outward of the body (49) of the in-ear device (45), the projection element (3) extending outward of the inner surface (7) of the intra-auricular support (2) can comprise or be substituted by the sound delivery element (50) of the in-ear device (45) and the flexible body (4) can be removably coupled to the sound delivery element (50) of the in-ear device (45). As to these embodiments, the passage (26) disposed in the flexible body (4) can be configured to insertingly receive, in part or the entirety, the sound delivery element (50) of in-ear device (45).

Now referring primarily to FIGS. 19 through 23, as to particular embodiments of the earpiece (1) which accommodate an in-ear device (45) having a sound delivery element (50) extending outward of the body (49), the an intra-auricular support conduit (46) can have an intra-auricular support conduit first end (51) disposed at the outer surface (6) of the intra-auricular support (2) and an intra-auricular support conduit second end (52) disposed at the inner surface (7) of the intra-auricular support (2). The intra-auricular support conduit internal surface (47) can be configured to releasably retain the body (49) of in-ear device (45) with the sound delivery element (50) extending outward of the inner surface (7) of the intra-auricular support (2). The intra-auricular support conduit passage (48) communicates from the outer surface (6) of the intra-auricular support (2) to the inner surface (7) of the intra-auricular support (2) and through the flexible body (4) to open at the flexible body second end (53) for the transmission of sound from the in-ear device (45) releasably retained at the intra-auricular support conduit first end (51) to the flexible body second end (53).

Now referring primarily to FIGS. 24 through 28, as to particular embodiments the intra-auricular support (2) can, but need not necessarily, include a tubular member (56) which extends a distance outward from the outer surface (6) of the intra-auricular support (2) to correspondingly dispose the intra-auricular support conduit first end (51) a distance outward of the outer surface (6) of the intra-auricular support (2). The intra-auricular support conduit internal surface (47) of the tubular member (56) can be configured to releasably retain the body (49) of the in-ear device (45). As to those in-ear devices (45) having a sound delivery element (50) extending a distance outward of the inner surface (7) of the intra-auricular support (2), the sound delivery element (50) extending outward of the intra-auricular support conduit internal surface (47) can be insertingly received in the flexible body (4) with the conduit passage (48) communicating from the outer surface (6) of the intra-auricular support (2) to the inner surface (7) of the intra-auricular support (2), through the flexible body (4) to open at the flexible body second end (53) for the transmission of sound from the in-ear device (45) releasably retained at the intra-auricular support conduit first end (51) to the flexible body second end (53).

As described above and again exemplified in FIGS. 17, 18, 22, 23, 27, and 28, particular embodiments of the earpiece (1) including an in-ear device (45) can include a moldable earpiece material (5) moldable about the intra-auricular support (2) to conform to the auricle (9) of the ear (10). The configuration of the embodiment shown in FIGS. 24 through 28 confers the advantage of molding the moldable earpiece material (5) around the tubular member (56) extending outward of the outer surface (6) of the intra-auricular support (2), thereby avoiding or reducing ingress of the amount of moldable earpiece material (5) in the intra-auricular support conduit passage (48) or in contact with the in-ear device (45).

Now referring to FIGS. 29 through 31, embodiments can, but need not necessarily include, a flexible elastomer insert (54) which removably couples to the intra-auricular support conduit (46) proximate the intra-auricular support conduit first end (51) to provide a flexible elastomer insert internal surface (55) configured to retain or releasably retain the in-ear device (45) in the intra-auricular support (2) or the earpiece (1). A plurality of flexible elastomer inserts (54) can provide a plurality of different configurations of the flexible elastomer internal surface (55) to retain or releasably retain a corresponding plurality of different configurations of the body (49) of the in-ear device (45). By interchanging the flexible elastomer insert (54) removably coupled within the intra-auricular support conduit (46) a plurality of different configurations of the flexible elastomer internal surface (55) can be achieved in one configuration of the intra-auricular support conduit (46), whereby a corresponding plurality of in-ear devices (45) of different configuration can be releasably retained. While the illustrative flexible elastomer insert shown in FIGS. 29-31 has a particular thickness, this is not intended to preclude embodiments of greater or lesser thickness and the thickness of particular embodiments can be as great as necessary to retain the in-ear device (45) in the intra-auricular support conduit (46) or the earpiece (1).

Now referring generally to FIGS. 1 through 31 and, more particularly to FIGS. 10, 11, and 12, a method of using the earpiece (1) can include obtaining an earpiece (1) including: an intra-auricular support (2), a projection element (3), a flexible body (4) disposed about the projection element (3), and a moldable earpiece material (5), disposing the flexible body (4) in the external ear canal (17) of an ear (10), adjusting the intra-auricular support (2) within the auricle (9) or concha bowl (15) having the intra-auricular support inner surface (7) disposed substantially adjacent the external ear canal opening (16), pressingly engaging the moldable earpiece material (5) about the intra-auricular support (2), conforming the moldable earpiece material (5) to the auricle (9) or the concha bowl (15) of the ear (10), and curing the moldable earpiece material (5) to provide a fixed configuration of the earpiece (1); the intra-auricular support (2), projection element (3), flexible body (4), and moldable earpiece material (5) having been described above.

In particular embodiments, as exemplified in FIGS. 17, 18, 22, 23, 27, and 28, a method of using the earpiece (1) may further include obtaining an intra-auricular support conduit (46) having an intra-auricular support conduit (46) configured to releasably retain an in-ear device (45), as described above, and releasably retaining an in-ear device (45) to the intra-auricular support conduit (46). As to particular embodiments, the method can further include releasably retaining a body (49) of an in-ear device (45) to the intra-auricular support conduit (46) with a sound delivery element (50) extending a distance outward of the inner surface (7) of the intra-auricular support (2), and removably coupling a flexible body (4) about the sound delivery element (50).

As can be easily understood from the foregoing, the basic concepts of the present invention may be embodied in a variety of ways. The invention involves numerous and varied embodiments of an earpiece which can be utilized for the production of an earpiece by the process above described.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of "a moldable earpiece material (5)" should be understood to encompass disclosure of the act of "molding an earpiece material"—whether explicitly discussed or not—and, conversely, were there effectively disclosure of the act of "molding an earpiece material", such a disclosure should be understood to encompass disclosure of "a moldable earpiece material (5)" and even a "means for molding an earpiece material." Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

Moreover, for the purposes of the present invention, the term "a" or "an" entity refers to one or more of that entity; for example, "an earpiece" refers to one or more of the earpieces. As such, the terms "a" or "an", "one or more" and "at least one" can be used interchangeably herein.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. The term "about" generally refers to a range of numeric values that one of skill in the art would consider equivalent to the recited numeric value or having the same function or result.

Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

Thus, the applicant(s) should be understood to claim at least: i) each of the earpieces herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

The claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

I claim:

1. An earpiece, comprising:
   an intra-auricular support, said intra-auricular support including:
      an outer surface opposite an inner surface each extending to an intra-auricular support peripheral edge, said intra-auricular support configured to contact and be retained in a concha bowl of an ear; and
   a moldable earpiece material moldable about said intra-auricular support to conform to said auricle of said ear, said moldable earpiece material curable in a fixed configuration of said earpiece conformed to said auricle of said ear.

2. The earpiece of claim 1, wherein said moldable earpiece material moldable about portions of said intra-auricular support which retain said intra-auricular support in said concha bowl of said ear.

3. The earpiece of claim 2, further comprising one or more aperture elements communicating between aid outer surface and said inner surface of said intra-auricular support.

4. The earpiece of claim 1, further comprising:
a projection element extending outward of said inner surface of said intra-auricular support; and
a flexible body disposed about said projection element, said flexible body configured to insert inside of an external ear canal of said ear concurrent with said intra-auricular support retained in said auricle of said ear.

5. The earpiece of claim 4, wherein said a flexible body disposed about said projection element removably couples to said projection element.

6. The earpiece of claim 5, further comprising a flexible body passage being disposed at said flexible body first end and extending from said flexible body first end toward said flexible body second end.

7. The earpiece of claim 6, further comprising a passage communicating from said outer surface of said intra-auricular support through said projection element and said flexible body, said passage open at a flexible body second end to transmit sound to said ear canal of said ear.

8. The earpiece of claim 7, wherein said passage communicating from said outer surface of said intra-auricular support configured to retain or releasably retain an in-ear device.

9. The earpiece of claim 8, wherein said in-ear device is selected from the group consisting of: earphones, earplugs, earbuds, ear tips, ear tubes, ear-sealing balloons, and in-ear hearing aids.

10. The earpiece of claim 8, wherein said in-ear device comprises a part of an apparatus which resides outside of said ear.

11. The earpiece of claim 10, further comprising selecting said apparatus which resides outside of said ear from the group consisting of: headsets, head phones, telephones, BLUETOOTH' headphones, wireless headphones, and hearing aids.

12. The earpiece of claim 1, further comprising an intra-auricular support conduit open between said inner surface and said outer surface of said intra-auricular support, said intra-auricular support conduit configured to retain or releasably retain an in-ear device.

13. The earpiece of claim 12, wherein said in-ear device has a body releasably retained by said intra-auricular support conduit and a sound delivery element, said sound deliver element extends outward of said intra-auricular support inner surface with said in-ear device retained by said intra-auricular support conduit.

14. The earpiece of claim 13, further comprising a flexible body disposed about said sound delivery element, said flexible body configured to insert inside of an external ear canal of said ear concurrent with said intra-auricular support retained in said auricle of said ear.

15. The earpiece of claim 14, further comprising a tubular member disposed about said intra-auricular support conduit and extending a distance outward from said inter-auricular support outer surface, said tubular member having a tubular member internal surface configured to releasably retain said in-ear device.

16. The earpiece of claim 15, further comprising a flexible elastomer insert having an elastomer insert external surface adapted to engage said tubular member internal surface, and having an elastomer insert internal surface configured to retain or releasably retain the in-ear device in the intra-auricular support of the earpiece.

17. The earpiece of claim 12, wherein said in-ear device is selected from the group consisting of: earphones, earplugs, earbuds, ear tips, ear tubes, ear-sealing balloons, and in-ear hearing aids.

18. The earpiece of claim 12, wherein said in-ear device comprises a part of an apparatus which resides outside of said ear.

19. The earpiece of claim 18, further comprising selecting said apparatus which resides outside of said ear from the group consisting of: headsets, head phones, telephones, BLUETOOTH' headphones, wireless headphones, and hearing aids.

20. The earpiece of claim 1, wherein said moldable earpiece material comprises a one-part moldable earpiece material.

21. The earpiece of claim 20, wherein said one-part moldable earpiece material is selected from the group consisting of: ethyl vinyl acetate, polycaprolactone, and room temperature vulcanization silicone.

22. The earpiece of claim 1, wherein said moldable earpiece material comprises a moldable agent combinable with a curing agent, said moldable agent combined with said curing agent curable to establish said fixed configuration of said earpiece.

23. The earpiece of claim 22, wherein said moldable agent and said curing agent comprises a crosslinkable polymer and a catalyst.

24. An earpiece comprising:
an intra-auricular support, said intra-auricular support including:
an outer surface opposite an inner surface each extending to an intra-auricular support peripheral edge, said outer surface or said inner surface having disposed on or in patterned surface elements, said intra-auricular support configured to contact and be retained in a concha bowl of an ear; and
a moldable earpiece material moldable about said intra-auricular support to conform to said auricle of said ear, said moldable earpiece material curable in a fixed configuration of said earpiece conformed to said auricle of said ear.

25. An earpiece comprising:
an intra-auricular support, said intra-auricular support including:
an outer surface opposite an inner surface each extending to an intra-auricular support peripheral edge, said intra-auricular support configured to contact and be retained in a concha bowl of an ear; and
a one-part moldable earpiece material moldable about said intra-auricular support to conform to said auricle of said ear, said moldable earpiece material curable in a fixed configuration of said earpiece conformed to said auricle of said ear, wherein said one-part moldable earpiece material comprises an amount of polycaprolactone polymer having a number average molecular weight of about 37,000 grams per mole to 80,000 grams per mole.

26. An earpiece comprising:
an intra-auricular support, said intra-auricular support including:
an outer surface opposite an inner surface each extending to an intra-auricular support peripheral edge, said intra-auricular support configured to contact and be retained in a concha bowl of an ear; and
a moldable earpiece material comprising a crosslinkable polymer and catalyst moldable about said intra-auricular support to conform to said auricle of said ear, said moldable earpiece material curable in a fixed configuration of said earpiece conformed to said auricle of said ear, wherein said crosslinkable polymer comprises a polymer containing at least one hydrolysable silane group and wherein said catalyst comprises one or more of a metallic salt of an organic carboxylic acid.

27. The earpiece of claim 26, wherein said crosslinkable polymer is selected from the group consisting of: a silane-modified olyoxyalkylene, a polyolefin, a poly(meth)acrylate, a polyurethane, a polyamide, and a polysiloxane and said metallic salt of an organic carboxylic acid, wherein said metallic salt of said organic carboxylic acid comprises one or more of a platinum, a tin or a copper salt of said organic carboxylic acid.

28. The earpiece of claim 27, wherein said crosslinkable polymer comprises polydimethylsiloxane and wherein said catalyst comprises platinum (0)-1,3-divinyl-1,1,3,3-tetramethyldisiloxane.

* * * * *